United States Patent
Pamplona et al.

(10) Patent No.: US 10,335,027 B2
(45) Date of Patent: Jul. 2, 2019

(54) METHODS AND APPARATUS FOR ASSESSMENT OF REFRACTIVE CONDITION

(71) Applicant: EyeNetra, Inc., Somerville, MA (US)

(72) Inventors: Vitor Pamplona, Somerville, MA (US); Ramesh Raskar, Cambridge, MA (US)

(73) Assignee: EYENETRA, INC., Cambridge, MA (US)

( * ) Notice: Subject to any disclaimer, the term of this patent is extended or adjusted under 35 U.S.C. 154(b) by 346 days.

(21) Appl. No.: 14/783,790

(22) PCT Filed: Apr. 10, 2014

(86) PCT No.: PCT/US2014/033693
§ 371 (c)(1),
(2) Date: Oct. 9, 2015

(87) PCT Pub. No.: WO2014/169148
PCT Pub. Date: Oct. 16, 2014

(65) Prior Publication Data
US 2016/0066780 A1    Mar. 10, 2016

Related U.S. Application Data

(60) Provisional application No. 61/810,429, filed on Apr. 10, 2013.

(51) Int. Cl.
*A61B 3/103* (2006.01)
*A61B 3/14* (2006.01)
(Continued)

(52) U.S. Cl.
CPC .......... *A61B 3/1035* (2013.01); *A61B 3/0008* (2013.01); *A61B 3/0025* (2013.01);
(Continued)

(58) Field of Classification Search
CPC ....... A61B 3/1035; A61B 5/6898; A61B 3/14; A61B 3/09; A61B 3/103; A61B 3/107;
(Continued)

(56) References Cited

U.S. PATENT DOCUMENTS 5,963,300 A * 10/1999 Horwitz ................. A61B 3/112
351/209
6,003,993 A * 12/1999 Webb ....................... A61B 3/14
351/221
(Continued)

FOREIGN PATENT DOCUMENTS

WO        2005024488 A1    3/2005

OTHER PUBLICATIONS

Mrochen et al., NPL—(Principles of Tscherning Aberrometry, Journal of Refractive Sugery, vol. 16, Oct. 2000).*
(Continued)

*Primary Examiner* — Evan P Dzierzynski
*Assistant Examiner* — Alberto J Betancourt
(74) *Attorney, Agent, or Firm* — Stephen R. Otis

(57) ABSTRACT

In exemplary implementations of this invention, an aberrometer is used to measure the refractive condition of any eye. An artificial light source emits light that travels to a light sensor. Along the way, the light enters and then exits the eye, passes through or is reflected from one or more spatial light modulators (SLMs), and passes through an objective lens-system. The SLMs modify a bokeh effect of the imaging system (which is only visible when the system is out-of-focus), creating a blurred version of the SLM patterns. The light sensor then captures one or more out-of-focus images. If there are refractive aberrations in the eye, these aberrations cause the SLM patterns captured in the images to be distorted. By analyzing differences between the distorted captured patterns and the undistorted SLM patterns, refrac-
(Continued)

tive aberrations of the eye can be computed and an eyewear measurement generated.

14 Claims, 18 Drawing Sheets

(51) Int. Cl.
    *A61B 5/00* (2006.01)
    *A61B 3/09* (2006.01)
    *A61B 3/00* (2006.01)

(52) U.S. Cl.
    CPC .............. *A61B 3/09* (2013.01); *A61B 3/14* (2013.01); *A61B 5/6898* (2013.01)

(58) Field of Classification Search
    CPC ..... A61B 3/158; A61B 3/0025; A61B 3/0008; A61B 3/1015; A61B 3/113; A61B 5/7246; A61B 3/0091; G02B 27/017; G02B 27/0172; G02B 2027/0138
    USPC ....... 351/221, 205–212, 222, 227, 228, 236, 351/239, 246; 359/370, 577; 345/8, 32; 348/207.1, 78; 382/103, 195; 600/356, 600/558, 587
    See application file for complete search history.

(56) References Cited

U.S. PATENT DOCUMENTS

| | | | |
|---|---|---|---|
| 6,631,991 B2 | 10/2003 | Wirth | |
| 6,781,681 B2 * | 8/2004 | Horwitz | A61B 3/0025 356/124.5 |
| 6,908,196 B2 | 6/2005 | Herekar et al. | |
| 7,690,789 B2 | 4/2010 | Dai et al. | |
| 8,409,178 B2 | 4/2013 | Dai et al. | |
| 2012/0212598 A1 | 8/2012 | Mowrey et al. | |
| 2013/0027668 A1 | 1/2013 | Pamplona et al. | |

OTHER PUBLICATIONS

Pamplona, NPL—(NETRA: Interactive Display for Estimating Refractive Errors and Focal Range, Oct. 12, 2012, http://cameraculture.media.mit.edu/netra).*

Howland, H., Photorefraction of eyes: history and future prospects. Optometry and Vision Science, Jun. 2009; vol. 86 No. 6, pp. 603-606.

Loibl, B., Hartmann tests on large telescopes carried out with a small screen in a pupil image. Astronomy and Astrophysics, vol. 91, No. 3, Nov. 1980, p. 265-268.

Platt, B. et al., History and principles of Shack-Hartmann wavefront sensing. Journal of Refractive Surgery, vol. 17 Sep./Oct. 2001, pp. S573-S577.

* cited by examiner

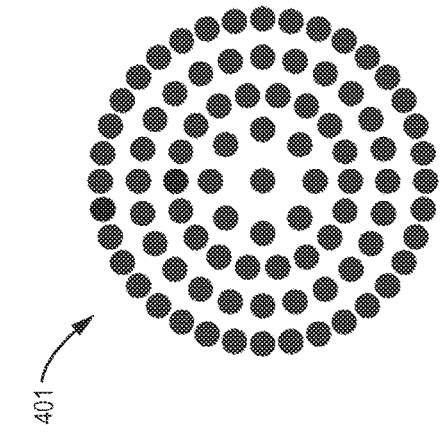
FIG. 4A
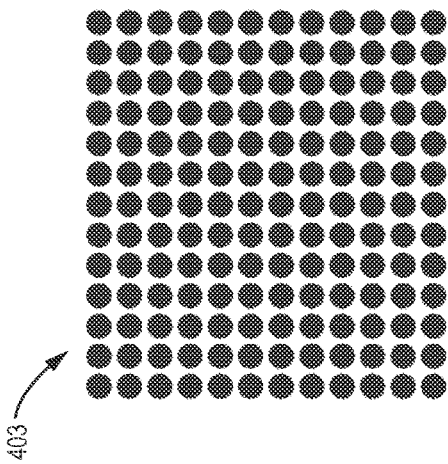
FIG. 4B
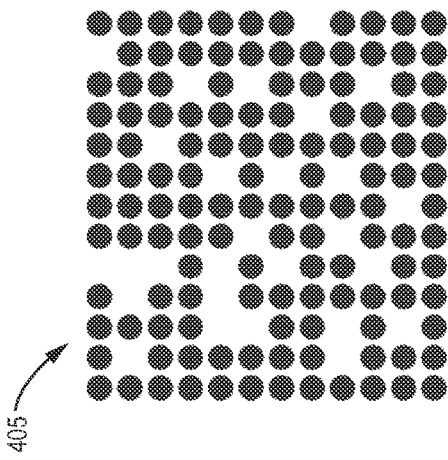
FIG. 4C
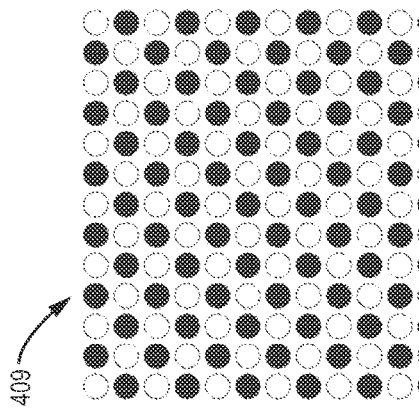
FIG. 4D
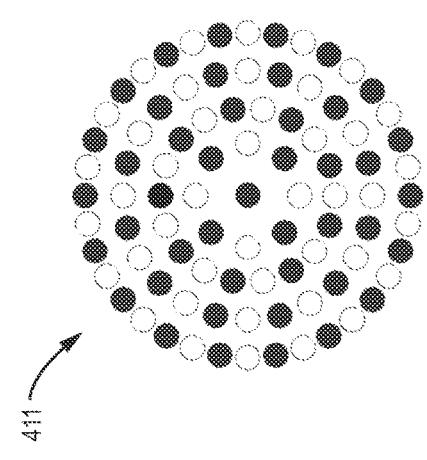
FIG. 4E
FIG. 4F

METHODS AND APPARATUS FOR ASSESSMENT OF REFRACTIVE CONDITION

RELATED APPLICATIONS

This application claims priority to the filing date of U.S. Provisional Application No. 61/810,429, filed Apr. 10, 2013, the entire disclosure of which is herein incorporated by reference.

FIELD OF THE TECHNOLOGY

The present invention relates generally to measurement of the refractive condition of an optical system. For example, the optical system being measured may comprise a lens or a human eye.

SUMMARY

In exemplary implementations of this invention, an aberrometer is used to measure the refractive condition of any eye. An artificial light source emits light, such that the light travels along a set of optical paths. The paths each start at the light source and end at a light sensor, and along the way each path enters and then exits the eye. As the light travels along the paths, it passes through or is reflected from one or more spatial light modulators (SLMs) that change an out-of-focus blur into a desired pattern. The light also passes through an objective lens-system that is optically between the eye and the light sensor.

The light sensor captures one or more images. If there are refractive aberrations in the eye, these aberrations cause the SLM patterns captured in the images to be distorted. By analyzing differences between the distorted captured patterns and the undistorted SLM pattern, the refractive aberrations of the eye can be computed and an eyewear measurement generated. One or more computer processors: (i) compute a first visual pattern, based at least in part on a pattern that appears in at least one of the images; (ii) compute a second visual pattern, based at least in part on a pattern displayed by a SLM; (iii) compute differences (e.g., distortions) between the first pattern and second pattern; and (iv) compute a refractive condition, based at least in part on the differences.

In some cases, the light source is collimated and an SLM is optically positioned between the light sensor and the eye. In those cases, the light sensor and each and every optical element that is optically between the light sensor and the eye can be considered to be a camera. In order to see the pattern, this camera is not focused on the first SLM and is not focused on the retina of the eye.

In other cases, a SLM is optically positioned between the light source and the eye. In those cases, the light may pass through a lens system that is optically between the light source and the eye and is optically in front of the first SLM. This lens system may have an optical power that prevents the eye from focusing on the SLM and from focusing on the light source.

In some implementations, the light may pass through more than one SLM.

In some embodiments, a camera (including an objective lens and light sensor) and one or more processors are housed in a mobile computing device. A SLM may be housed in a device that is releasably attached to the mobile computing device.

In exemplary embodiments, this invention may be used to measure a wide variety of refractive aberrations, including myopia, hyperopia, astigmatism, or higher order aberrations. Alternately, in some cases, this invention may be used as a lensometer to measure the refractive condition of a lens or other artificial optical system.

The description of the present invention in the Summary and Abstract sections hereof is just a summary. It is intended only to give a general introduction to some illustrative implementations of this invention. It does not describe all of the details of this invention. This invention may be implemented in many other ways.

BRIEF DESCRIPTION OF THE DRAWINGS

In FIG. 1A, a spatial light modulator (SLM) is in front of a focusing lens. In FIG. 1B, a SLM is behind the focusing lens.

In FIG. 2A, a SLM is in front of a focusing lens. In FIG. 2B, a SLM is behind the focusing lens.

In FIG. 3A, a SLM is in front of a focusing lens. In FIG. 3B, a SLM is in front of a focusing lens, and a zoom lens is between them. In FIG. 3C, a SLM is behind a focusing lens.

FIGS. 4A, 4B, 4C, 4D, 4E and 4F show examples of patterns that: (1) can be displayed by an SLM in the aberrometer; and (2) and can have a high frequency in the Fourier domain.

FIG. 4A shows a radial pattern. FIG. 4B shows a grid pattern. FIG. 4C shows a random pattern. FIG. 4D shows a pattern of different colors. (The colors are symbolized in FIG. 4D by different levels of gray). FIG. 4E shows a "checkerboard" grid pattern. FIG. 4F shows a "checkerboard" radial pattern.

FIG. 5A shows the undistorted pattern. FIG. 5B shows the pattern, after being distorted by a −2 Diopter myopic eye. FIG. 5C shows the pattern, after being distorted by a −6 Diopter astigmatic eye.

FIG. 6A shows distortion by a 1 diopter myopic eye. FIG. 6B shows distortion by a 4 diopter myopic eye. FIG. 6C shows distortion by a 10 diopter myopic eye. FIG. 6D shows distortion by a 20 diopter myopic eye.

FIG. 7A shows distortion by an eye with 45 degrees astigmatism. FIG. 7B shows distortion by an eye with 90 degrees astigmatism. FIG. 7C shows distortion by an eye with 130 degrees astigmatism.

In FIG. 8A, a lens is between the light sensor and the SLM. In FIG. 8B, an SLM is betwen the lens and the SLM.

In FIG. 12, the GUI displays a "Welcome to the eye test application" message. In FIG. 13, the GUI displays a message indicating that the eye test is in progress. In FIG. 14 the GUI displays eye test results.

The above Figures show some illustrative implementations of this invention, or provide information that relates to those implementations. However, this invention may be implemented in many other ways. The above Figures do not show all of the details of this invention.

DETAILED DESCRIPTION

In exemplary embodiments of this invention, an aberrometer measures refractive aberrations in a human eye. The aberrometer may comprise a camera with an SLM in front of the aperture. The camera takes a picture of a pattern that has been illuminated from a virtual source inside the patient's eye. As the required correction power increases (i.e., to correct for myopia, hyperopia, presbyopia or astigmatism), the pattern captured by the sensor scales or deforms. One or more computer processors analyze the size and shape of the captured pattern relative to the original pattern, in order to calculate the refractive correction required for myopia, hyperopia, astigmatism and higher-order aberrations.

Figure 1A:
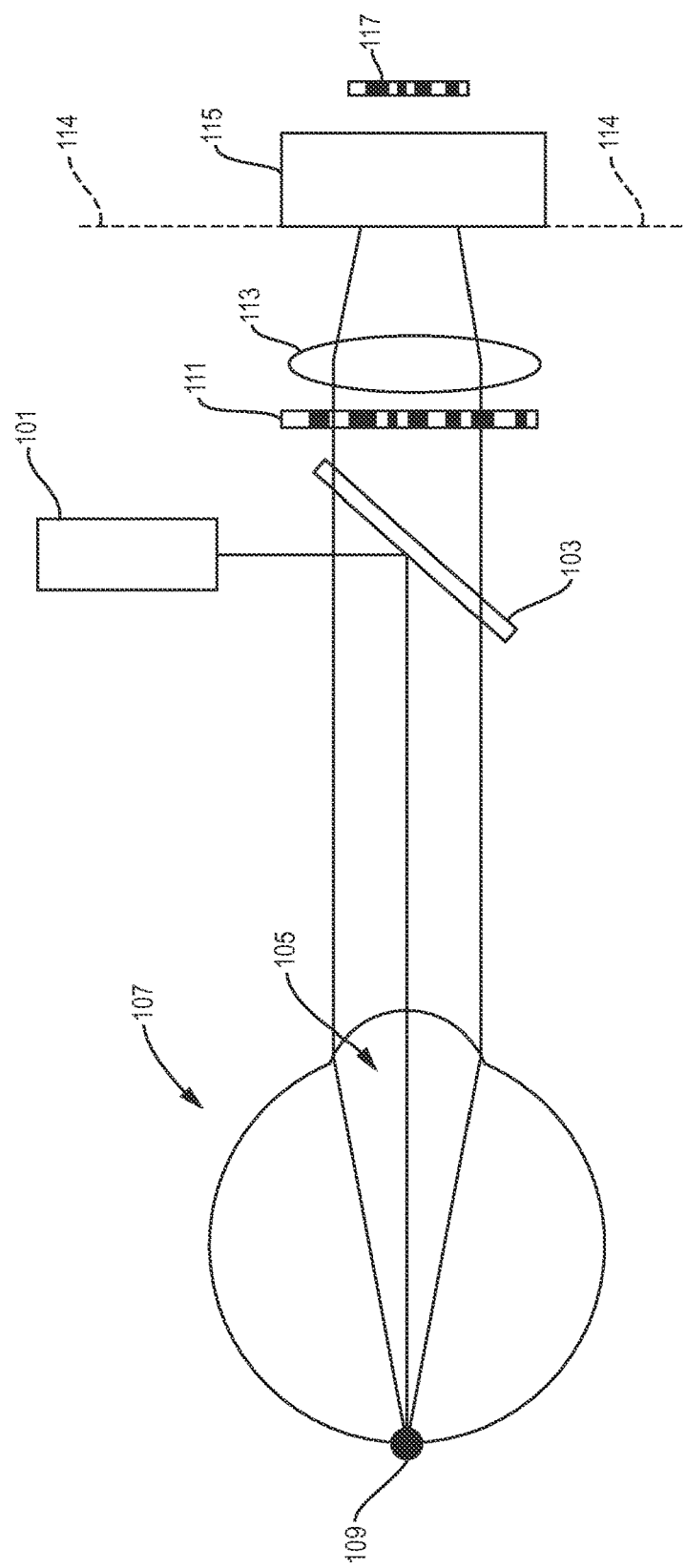
FIGS. 1A and 1B show an aberrometer with a collimated light source, measuring an emmetropic eye.
Figure 1B:
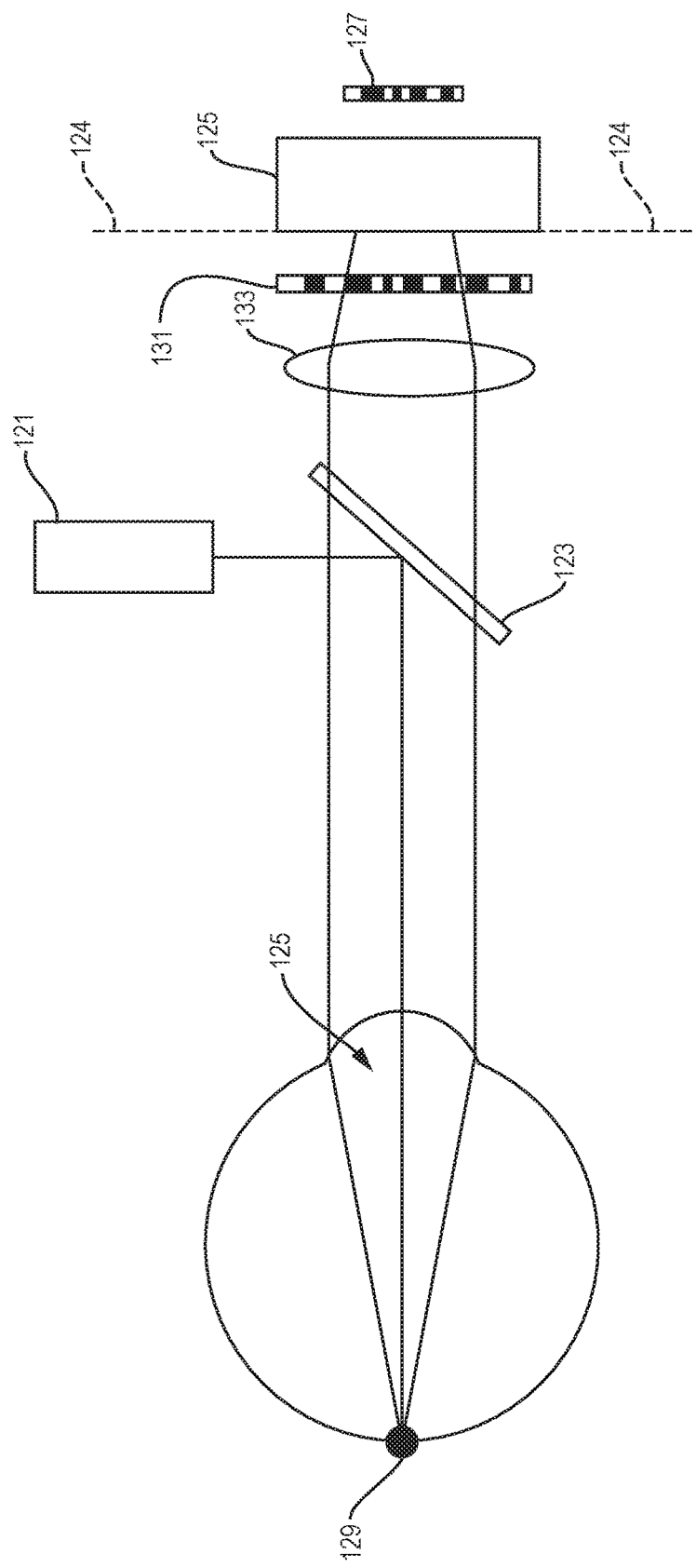

FIGS. 1A and 1B show an aberrometer with a collimated light source, measuring an emmetropic eye. In the examples shown in FIGS. 1A and 1B: light from a collimated light source 101, 121 is reflected by a beamsplitter 103, 123 and then travels through the pupil 105, 125 of an emmetropic human eye 107 to a small point 109, 129 on the retina of the eye. The light reflects back out of the pupil 105, 125 of the eye. After the light leaves the eye, it travels through the beamsplitter 103, 123, a spatial light modulator (SLM) 111, 131 and an objective lens-system 113, 133 to a light sensor 115, 135.

For example, the SLM 111, 131 may comprise an optical mask. The SLM may display a spatial light attenuation pattern that does not vary over time. Alternatively, the SLM may display a spatial light attenuation pattern that varies over time.

The light sensor captures a pattern 117, 127 that is a scaled (in this case, smaller) version of a portion (but not all) of the original light attenuation pattern displayed by the SLM. The remainder of the original pattern is not captured, due to cropping by the camera's aperture.

The viewing angle of the captured pattern can give an estimate for the patient's pupil size. The bigger the viewing angle of the SLM, the bigger the pupil size. By computing where the captured image is cropped in relation to the SLM, one can estimate where the light is coming from and, since it is reflecting from the retina, the eye's pupil. The relation between the pattern crop size (L) and the pupil radius (R) can be defined by:

$$L = R - cRt$$

where c is the spherical equivalent of the computed prescription and t is the distance from the eye to the SLM. The aberrometer may touch the patient's face, in which case t is known.

The positions of the SLM and objective lens-system are different in FIGS. 1A and 1B. In FIG. 1A, the SLM 111 is in front of the objective lens-system 113; whereas, in FIG. 1B, the SLM 131 is behind the objective lens-system.

As used herein, A is in "front" of B, if A is optically closer to the eye than is B (i.e. the optical distance between A and the eye is less than the distance between B and the eye). As used herein, A is "behind" B, if A is optically further from the eye than is B (i.e. the optical distance between A and the eye is greater than the distance between B and the eye).

In some embodiments of this invention, an aberrometer includes a collimated light source and a coded aperture sensor. The light projects a point source into the eye. The light reflects back from the retina, leaves the eye through the pupil, and reaches a coded sensor (e.g., a light sensor behind a SLM). The image captured by the sensor is a distorted version of an in-focus image of the pattern displayed by the SLM. One or more computer processors compute the distortions of the captured pattern relative to the original version, and, based on the computed distortion, calculate the refractive condition of the eye. Preferably, the aberrometer is positioned, during operation, close to the eye such that brightness and angular resolution are increased. Side-by-side lens arrays can be used in conjunction or independent of the SLM to capture more light from the optical system (e.g., eye or lens) being measured.

During the measurement, the patient may fluctuate his accommodative/focal state. The aberrometer can capture several images, compute the required power for all of them and use the most positive value as a measurement of the refractive condition of the eye. Alternatively, averages, weighted sums or other statistical methods can be applied to the computed powers.

In exemplary implementations, the aberrometer can capture reliable data without the need for eye drops. Preferably, during this test, the patient's eye is focusing at the maximum distance possible for the patient, in order to achieve the most relaxed state of the crystalline lens. A half-mirror system can be used to make the person look to the far field while being measured with the device, or a simple instruction can be given, asking the patient to try to focus on a distant point.

Figure 2A:
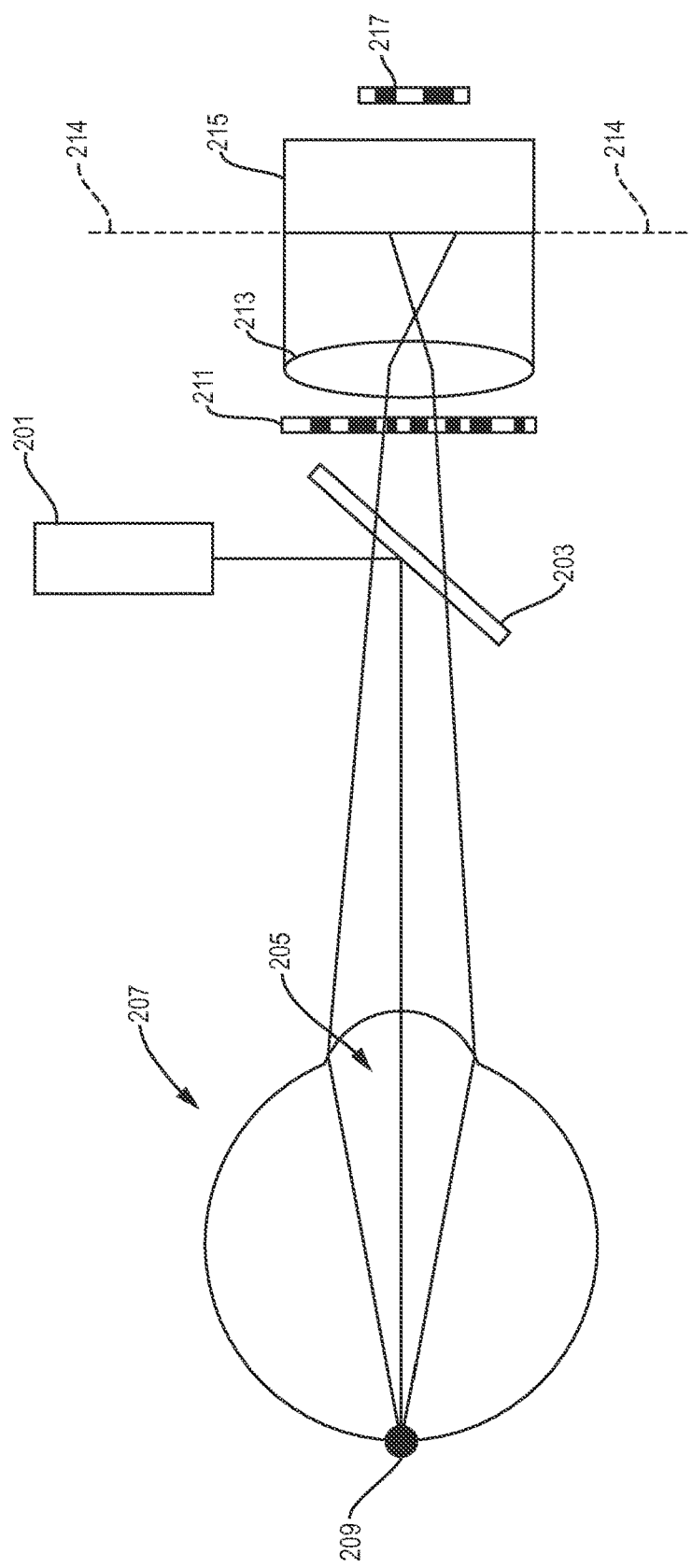
FIGS. 2A and 2B show an aberrometer with a collimated light source, measuring a myopic eye.
Figure 2B:
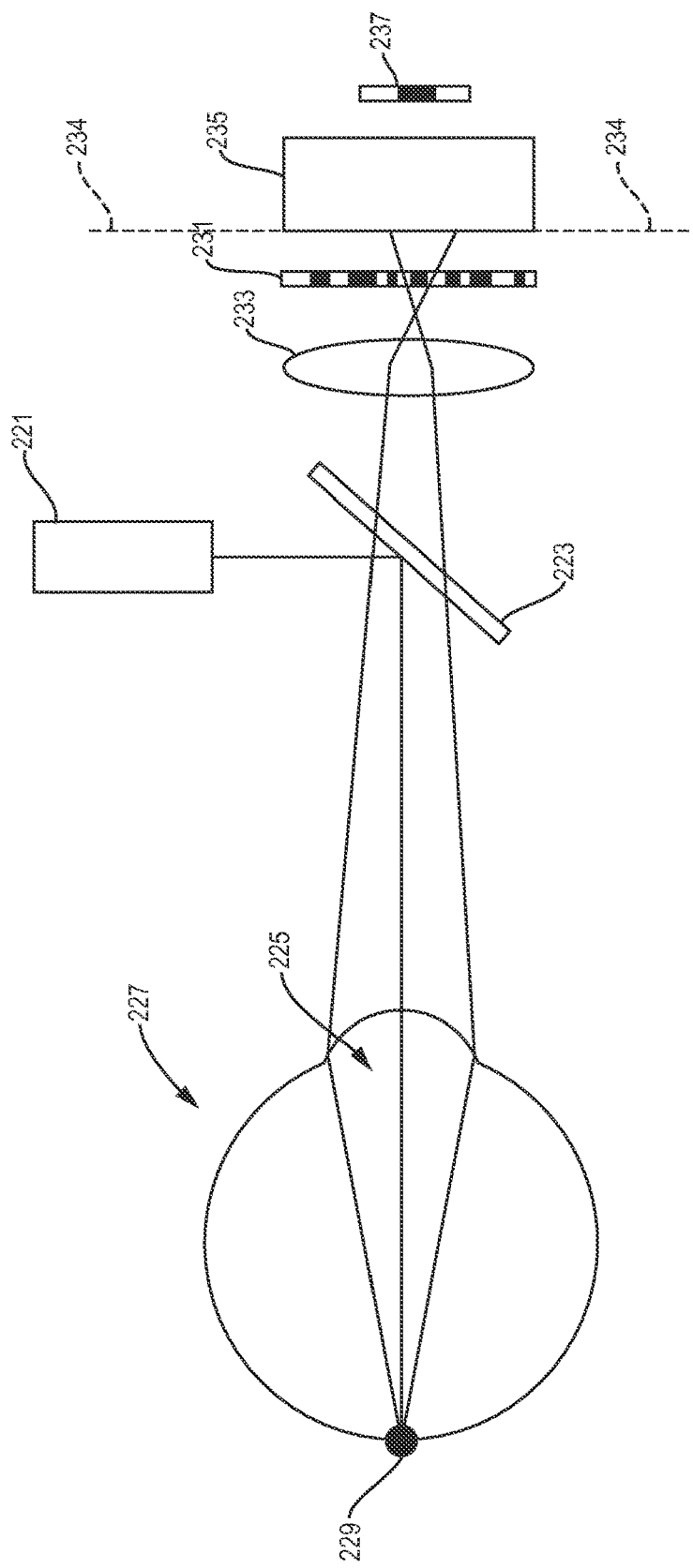

FIGS. 2A and 2B show an aberrometer with a collimated light source, measuring a myopic eye.

FIGS. 2A and 2B are the same as Figures 1A and 1B, respectively, except that the aberrometer is imaging a myopic eye, rather than an emmetropic eye. Because the myopic eye cannot focus far, the light converges at a point before the light sensor plane 214, 234 and the captured image becomes scaled. The scaling factor is proportional to the correction required to give the individual normal eyesight In the examples shown in FIGS. 2A and 2B: light from a collimated light source 201, 221 is reflected by a beamsplitter 203, 223 and then travels through the pupil 205, 1225 of a myopic human eye 207, 227 to a small point 209, 229 on the retina of the eye. The light reflects back out of the pupil 205, 225 of the eye. After the light leaves the eye, it travels through a SLM 211, 231 and an objective lens-system 213, 233 to a light sensor 215, 235. The light sensor captures a pattern 217, 237 that is a scaled (in this case, larger) version of a portion (but not all) of the original light attenuation pattern displayed by the SLM. The remainder of the original pattern is not captured, due to cropping from the camera's own aperture.

In the examples shown in FIGS. 1A, 1B, 2A, 2B, a collimated light source creates a bright point on the retina. For example, the collimated light can be a short pulse of laser of a given light frequency. Or, for example, the collimated light source may comprise an optical system that includes a non-directional light source (e.g., an LED) that shines light through collimating optics (e.g., through a a double pinhole SLM or through a lens that is one focal length from the non-directional light source). In these examples, the captured image is the light intensity modulated by the pattern that is in front of the sensor. Other embodiments can emit and capture multiple light frequencies, increasing the accuracy of the assessment.

In FIGS. 1A, 1B, 2A, 2B, and 3A, a dashed line 114, 124, 214, 234, 314 represents the sensor plane of a light sensor.

The beam splitter can remove reflections from the cornea. For example, a polarized beam splitter can block the polarized reflection onto the cornea while allowing the light from the retina goes through.

In some implementations, the light source can be a broadband white LED (all frequencies represented in a known factor), and the sensor is wavelength dependent (capturing color and/or other frequencies outside the visible spectrum). The captured image may be decomposed from the sensor's frequency groups (e.g. RGB pixels) and be used to estimate the corrective refraction needed at given wavelengths, increasing accuracy of the technique. The same technique can measure differences in chromatic aberration among subjects and refine the refractive correction for them.

However, the examples shown in FIGS. 1A, 1B, 2A and 2B require a collimated light source. If a white broadband LED is used in these examples, then light from the LED is transmitted through collimating optics, as described above.

The SLMs can be built with any opaque/transparent set of patterns or semi-transparent materials, such as color films or lithography. They can also be electronic and use polarization or diffraction effects to simulate the code, such as translucent displays like LCDs or semi-transparent OLEDs. Electronic SLMs can display different patterns over time and thereby increase the amount of samples, increasing accuracy of the technique.

The pattern of the SLM can be anything: a binary image, a gray scale pattern or a full color film. It is a tradeoff between simplicity and robustness of the device. Binary images are the easiest to process and they can reliably measure myopia, hyperopia and astigmatism. Gray scale patterns add more information to the captured image, enhancing accuracy and resolution.

In some implementations of this invention, color filters in an SLM measure not only refractive conditions but also the individual's color deficiencies. Color filters allow sampling of a group of wavelengths. If there is a shift in the proportion between these wavelengths, the patient may have a color deficiency (when the absorption is greater in certain wavelengths). Patterns that have the most features in the frequency spectrum (i.e., in the Fourier domain) are preferable. Since only a fraction of the light gets reflected by the retinal layer, the same device can measure light absorption of the rods and cones by accounting for an absorption factor per wavelength of light, allowing the device to measure and screen for color vision deficiencies.

Figure 3A:
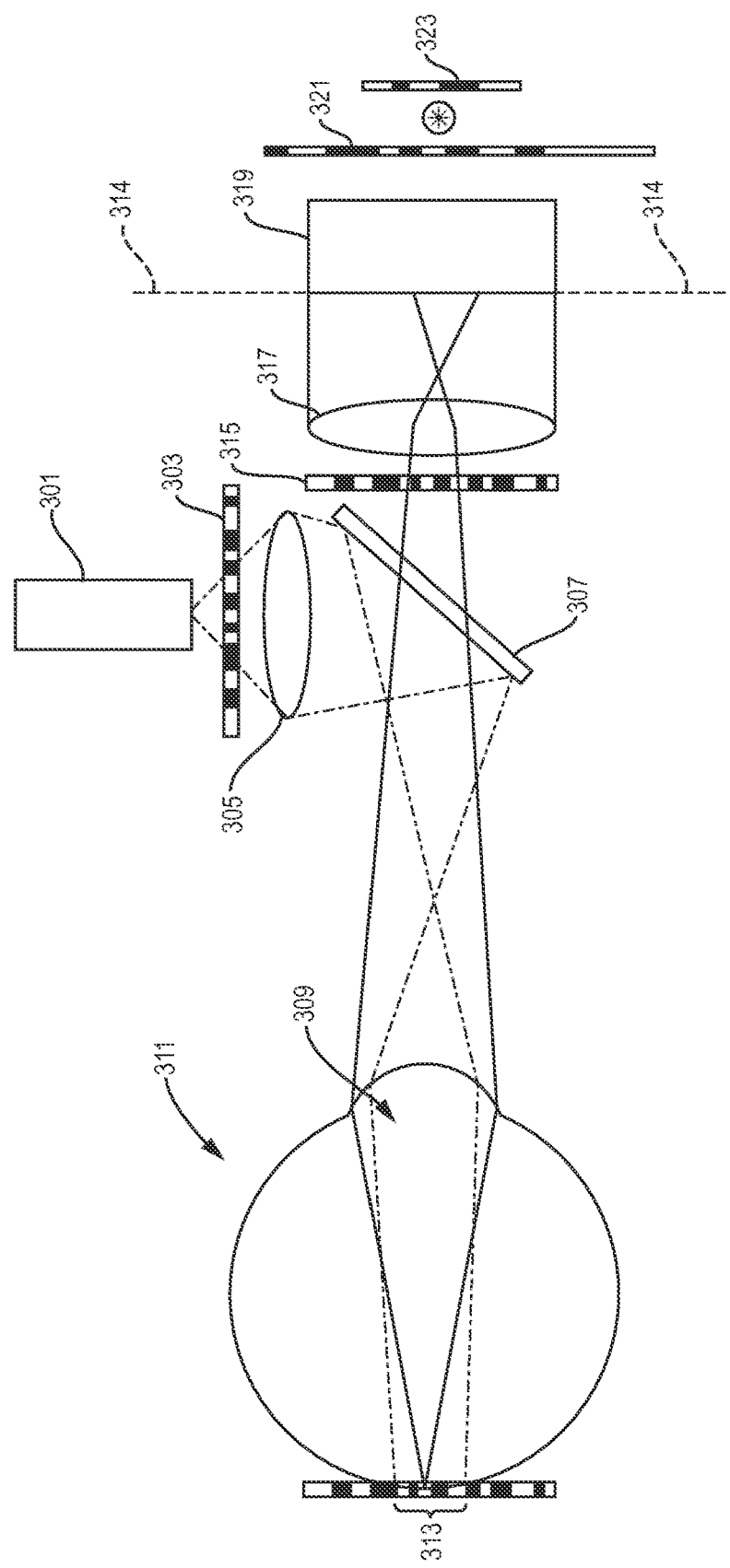
FIGS. 3A, 3B and 3C show an aberrometer with an uncollimated light source.
Figure 3B:
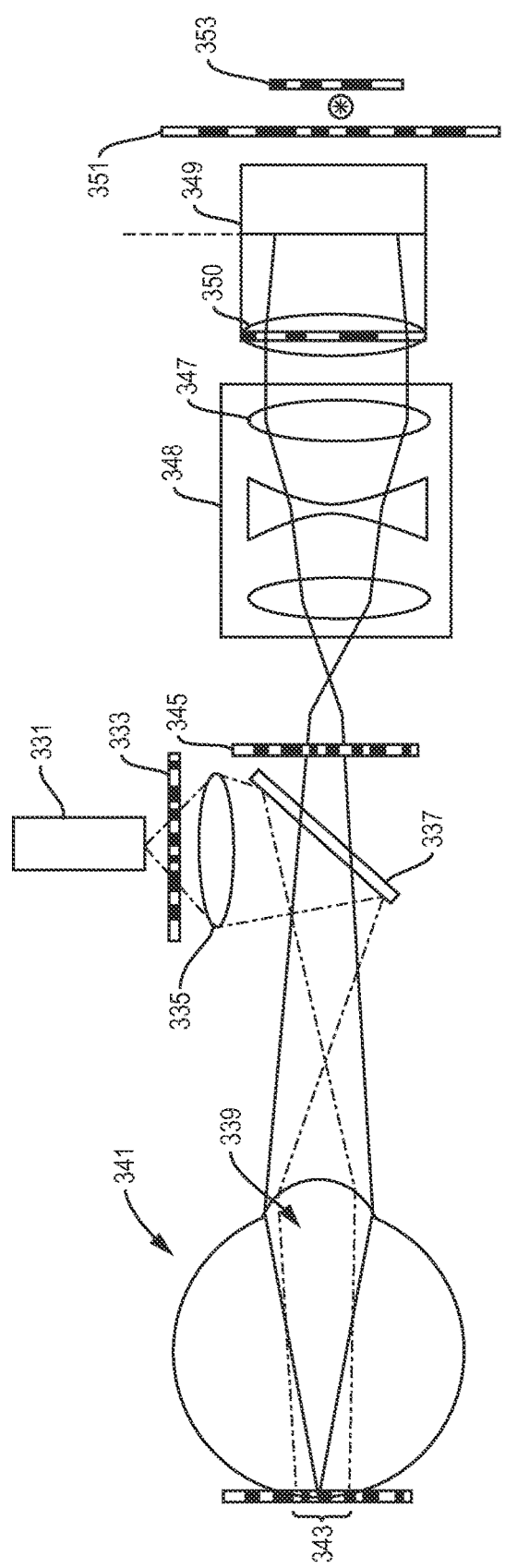
Figure 3C:
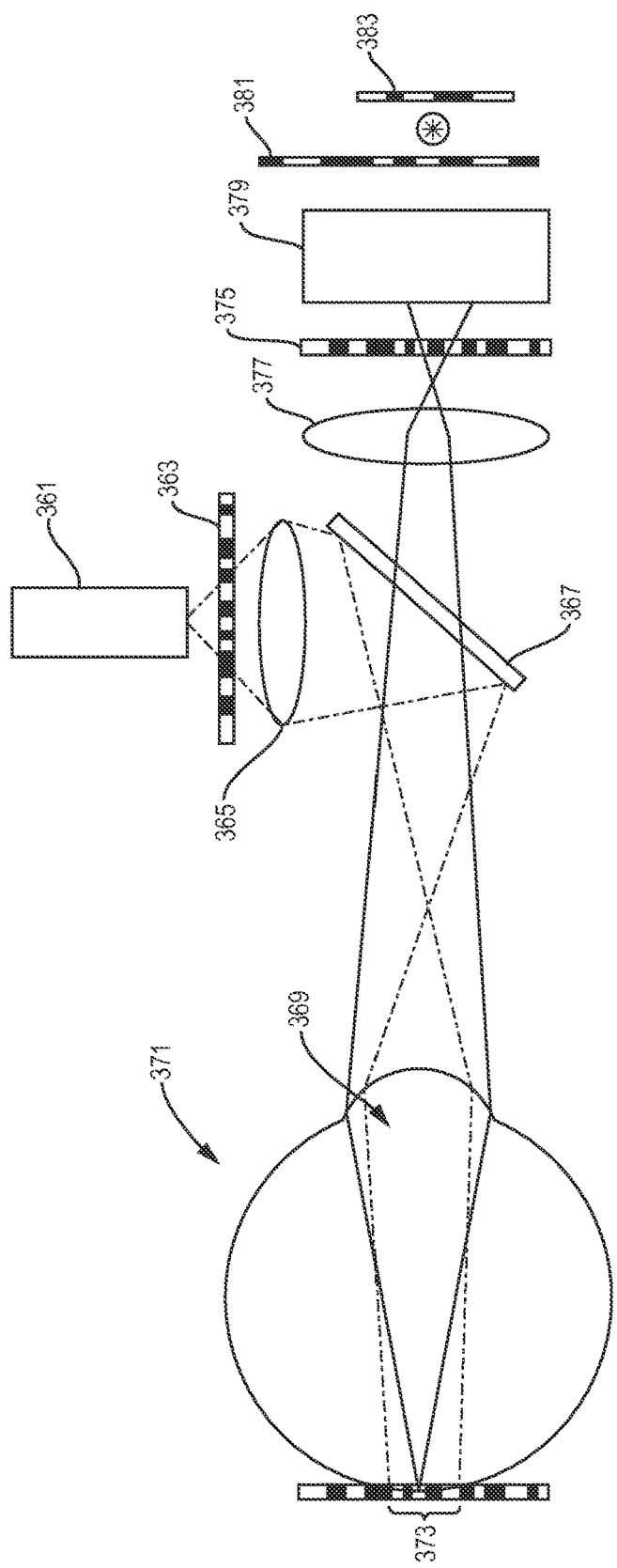

FIGS. 3A, 3B and 3C each show an aberrometer that has an uncollimated light source. In the examples shown in FIGS. 3A, 3B and 3C, there are two SLMs in the optical path between the light source and the light sensor. The first SLM 303, 333, 363 is positioned between the eye 311, 341, 371 and the uncollimated light source 301, 331, 361. The second SLM 315, 345, 375 is positioned between the eye 311, 341, 371 and the light sensor 319, 349, 379.

Uncollimated light travels from the light source 301, 331, 361, and through the first SLM 303, 333, 363 and a lens system 305, 335, 365, then reflects off a beamsplitter 307, 337, 367, and then travels through the pupil 309, 339, 369 of the eye 311, 341, 371 to the retina of the eye, creating a light pattern 313, 343, 373 on the retina. The light reflects off the retina, then travels through the pupil 309, 339, 369, the beamsplitter 307, 337, 367, the second SLM 315, 345, 375 and an objective lens-system 317, 347, 377, and then travels to a light sensor 319, 349, 379.

In the examples shown in FIGS. 3A, 3B, 3C, a light pattern 313, 343, 373 is formed on the retina, due to the coding on the light source (i.e., due to the first SLM 303, 333, 363). This retinal light pattern 313, 343, 373 is a blurry version of a portion of the modulation pattern of the first SLM 303, 333, 363. It is blurry because lens system 305, 335, 365 has an optical power that makes it impossible for the eye to focus on the first SLM 303, 333, 363 and impossible for the eye to focus on the light source 301, 331, 361.

The light sensor captures a pattern that can be defined as a convolution of a first pattern 321, 351, 381 and a second pattern 323, 353, 383, where (a) the first pattern 321, 351, 381 is a blurry version of a portion of the modulation pattern of the second SLM 315, 345, 375; and (b) the second pattern 323, 353, 383 captures a portion of the retinal light pattern 313, 343, 373. In some implementations, before the convolution is performed, the first and second patterns are scaled or otherwise transformed.

In the examples shown in FIGS. 3A, 3B, and 3C, the light sensor and the lens(es) between the eye and the light sensor may, together, be considered a camera. The second pattern 323, 353, 383 is blurry because this camera is not focused on the second SLM 315, 345, 375 and is not focused on the retina.

In the example shown in FIG. 3B, a zoom lens system 348 includes multiple lenses that, together, magnify the image and converge light. For example, zoom lens 348 and light sensor 349 may be housed in a mobile computing device (MCD).

In FIG. 3B, image 350 conceptually illustrates the shape, at image 350's position in the optical stack, of the light pattern created by the second SLM 345. Image 350 illustrates the magnifying effects of the zoom lens system 348 on that light pattern. The image size is increased by the zooming system and the camera only captures the central part of the SLM. Since two SLMs are present in this example, one coding the light and another coding the camera, the result is a convolution of patterns 351 and 353.

The positions of the second SLM and objective lens-system are different in FIG. 3C than they are in FIGS. 3A and 3B. SLM 315, 345 is in front of objective lens-system 317, 347 in FIGS. 3A and 3B; whereas SLM 375 is behind objective lens-system 377 in FIG. 3C.

In the examples shown in FIGS. 3A, 3B and 3C, a non-directional light source 301, 331, 361 and two SLMs are used. The first SLM 303, 333, 363 creates a pattern in the retina, such as a circle or other two dimensional pattern. (This is unlike FIGS. 1A, 1B, 2A, 2B, where collimated light illuminates a point 109, 119, 209, 229 on the retina.) The final captured image S is a convolution: S=DLD'M, where L is the pattern of the first SLM, M is the pattern of the second SLM, and D and D' are transformation matrixes.

Alternatively, the second SLM 315, 345, 375 may be omitted. In that case, the image S captured by the sensor will be the pattern of the first SLM 303, 333, 363 deformed by the eye lens aberrations: S=DL.

In the examples shown in FIGS. 3A, 3B and 3C, a standard light bulb or LED is used as an uncollimated light source. A modulation pattern of the first SLM 303, 333, 363 is projected onto the retina after being deformed (scaling or stretching) by the subject's refractive condition. By changing the distances between components and focal lengths of the lenses, an aberrometer can be built in such a way that a single dot is projected into the retina if the person has no need for glasses.

FIGS. 4A, 4B, 4C, 4D, 4E and 4F show examples of patterns that can be displayed by an SLM in the aberrometer.

FIG. 4A shows a radial pattern 401. FIG. 4B shows a grid pattern 403. FIG. 4C shows a random pattern 405. FIG. 4D shows a pattern of different colors 407. (The colors are symbolized in FIG. 4D by different levels of white, gray and black). FIG. 4E shows a "checkerboard" grid pattern 409. FIG. 4F shows a "checkerboard" radial pattern 411.

An SLM pattern of different colors can be used for detecting color vision deficiencies, as follows: The color patterned SLM can code light into groups of wavelengths and filter the groups of wavelengths independently. As a result, the captured image includes data about the pixel intensity for each color at each retinal position. Using this data, one or more computer processors can compute a relative measurement of how much light the retina is absorbing per wavelength group and per retinal position, and thus to identify color vision deficiencies distributed in the retina.

For example, a white light may be used to create a dot onto the retina (e.g., the fovea) and the camera may be coded with a colored pattern. In that case, the captured image will be attenuated according to the absorption profile of a single spot in the retina. This allows the processor to compute a relative measurement of how much light that particular retinal position is absorbing and thus identify color vision deficiencies. In cases where the camera sensor already has color filters, a SLM can code distinct groups of wavelengths from the color filters on the sensor. This allows the processor to decompose the captured colors into smaller groups of wavelengths.

For example, colored pattern 407 could be used for assessing color deficiencies. (In FIG. 4D, the different colors of the colored pattern are symbolized by different shades of white, gray and black).

Figure 5C:
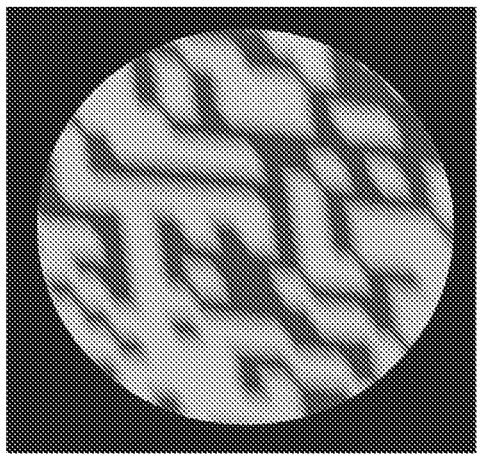
FIG. 5A, 5B and 5C are photographs that show examples of how an SLM pattern can be deformed by different aberrations of an eye, when imaged by the aberrometer.
Figure 5B:
Figure 5A:
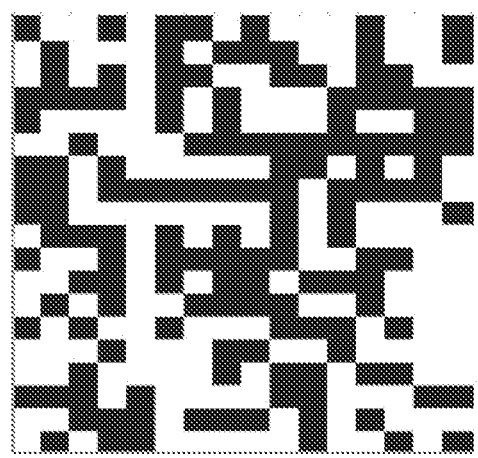

FIG. 5A, 5B and 5C are photographs that show examples of how an SLM pattern can be deformed by different aberrations of an eye, when imaged by the aberrometer. FIG. 5A shows the undistorted pattern. FIG. 5B shows the pattern, after being distorted by a −2 Diopter myopic eye. FIG. 5C shows the pattern, after being distorted by a −6 Diopter astigmatic eye. As the number of aberrations increase (coma, keratoconus, etc) the image deforms non-linearly.

Figure 6A:
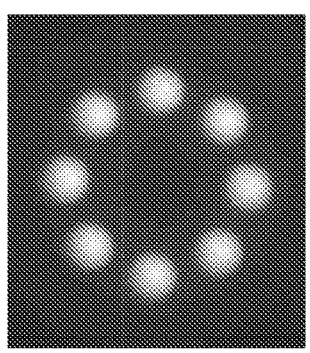
FIGS. 6A, 6B, 6C and 6D are photographs that show examples of how a binary SLM with a circle of pinholes can be distorted by myopic aberrations of an eye, when imaged by the aberrometer.
Figure 6B:
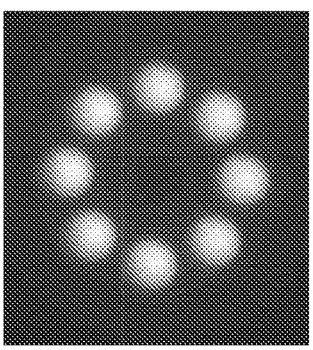
Figure 6C:
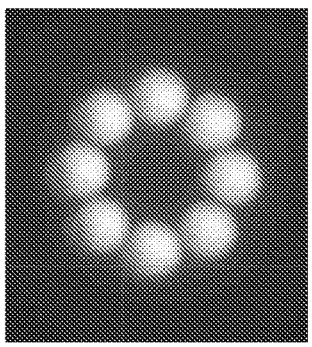
Figure 6D:
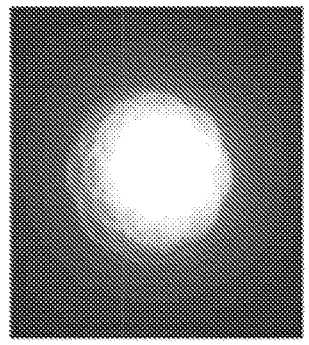

FIGS. 6A, 6B, 6C and 6D are photographs that show examples of how a binary SLM with a circle of pinholes can be distorted by myopic aberrations of an eye, when imaged by the aberrometer. FIG. 6A shows distortion by a 1 diopter myopic eye. FIG. 6B shows distortion by a 4 diopter myopic eye. FIG. 6C shows distortion by a 10 diopter myopic eye. FIG. 6D shows distortion by a 20 diopter myopic eye. As the aberration increases, the circle of patterns gets smaller. The computational procedure uses each pinhole as an image feature and builds the transformation matrix.

Figure 7A:
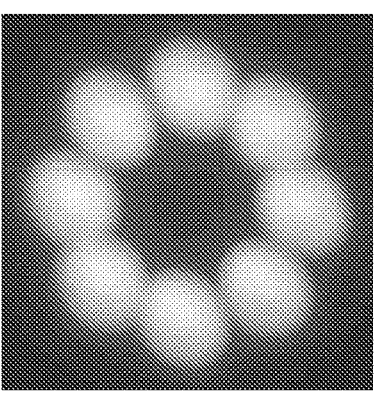
FIGS. 7A, 7B, and 7C are photographs that show examples of how a binary SLM with a circle of pinholes can be distorted by astigmatic aberrations of an eye, when imaged by the aberrometer.
Figure 7B:
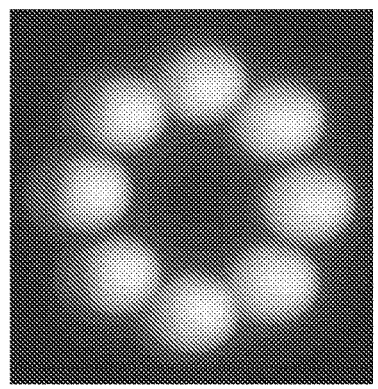
Figure 7C:
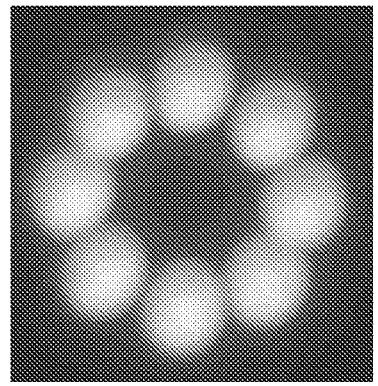

FIGS. 7A, 7B, and 7C are photographs that show examples of how a binary SLM with a circle of pinholes can be distorted by astigmatic aberrations of an eye, when imaged by the aberrometer. FIG. 7A shows distortion by an eye with 45 degrees astigmatism. FIG. 7B shows distortion by an eye with 90 degrees astigmatism. FIG. 7C shows distortion by an eye with 130 degrees astigmatism. The circle of patterns transforms into an ellipse and its two main diameters are proportional to the spherical and cylindrical powers. The ellipse rotates with the aberration axis. The computational procedure uses each pinhole as an image feature and builds the transformation matrix.

Figure 8A:
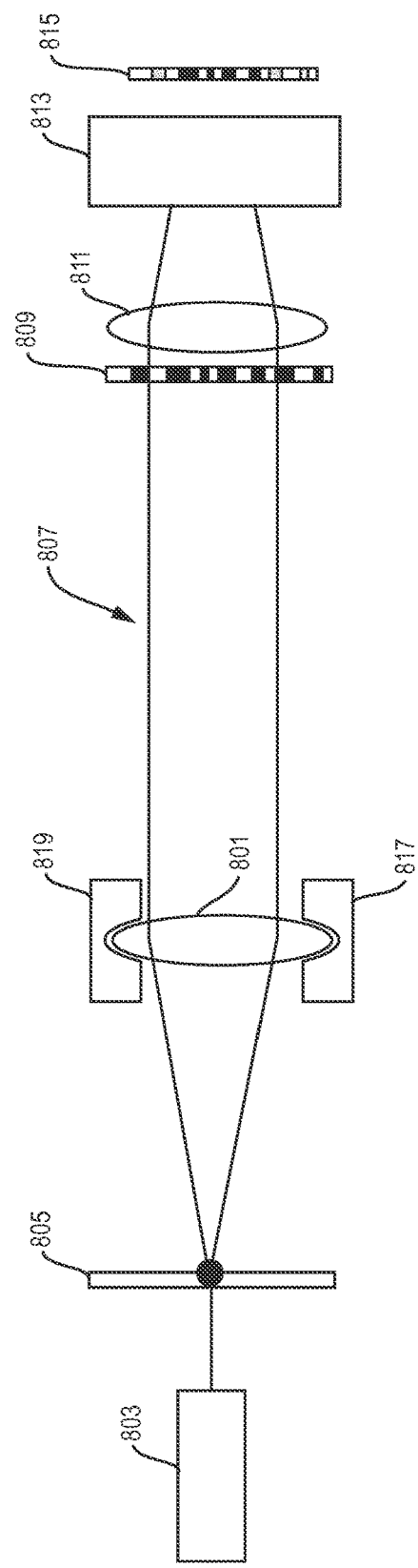
FIGS. 8A and 8B show an aberrometer for measuring aberrations of a lens.
Figure 8B:
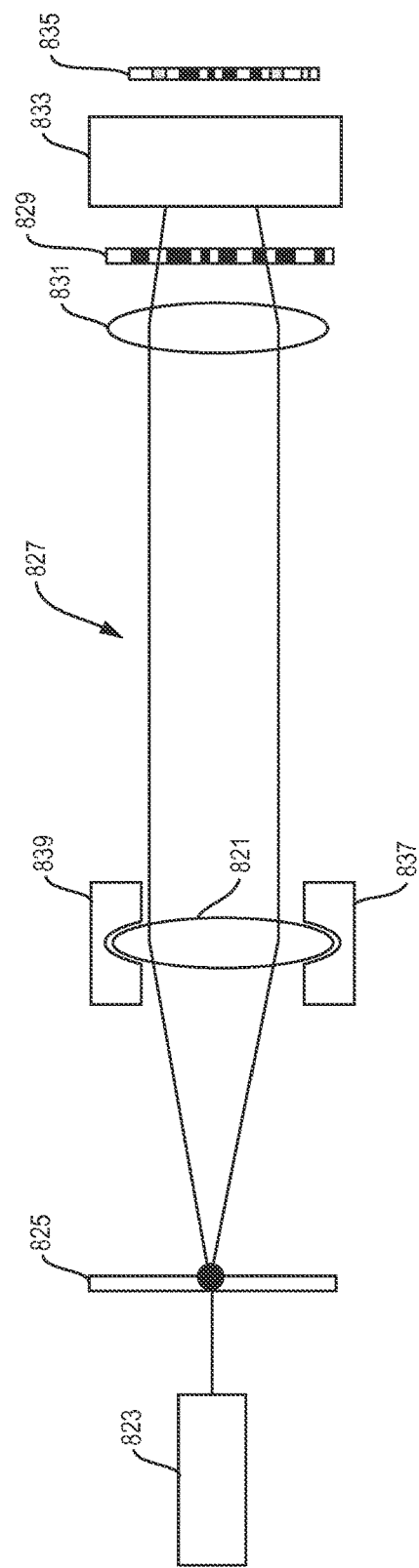

FIGS. 8A and 8B show an aberrometer being used as a lensometer. In these examples, the aberrometer measures refractive condition (e.g., optical power) of a lens.

In the examples shown in FIGS. 8A and 8B, a collimated light source 803, 823 shines light onto a point on the diffuser 805, 825. The diffuser scatters the light equally throughout the lens diameter.

The diffused light passes through the lens 801, 821 that is being assessed. This lens 801, 821 is held in place by a pair of supports (817, 819 in FIG. 8A, 837, 839 in FIG. 8B). In this example, the light rays (e.g., 807, 827) are collimated when they exit the test lens. However, in some other implementations, the light rays are not collimated at this point in the optical path. The light passes through a SLM 809, 829 and an objective lens-system 811, 831 before impacting a light sensor 813, 833. The light sensor captures a blurry image 815, 835 of a portion of the pattern displayed by the SLM 809, 829. The image 815, 835 is blurred because the light sensor 813, 833 and objective lens-system 811, 831 are not focused on the SLM 809, 829 and are not focused on the diffuser 805, 825.

FIGS. 8A and 8B show different positions for the SLM 809, 829. The SLM 809 is in front of the objective lens-system 811 in FIG. 8A; whereas the SLM 829 is behind the objective lens-system 831 in FIG. 8B.

In exemplary implementations of this invention, an out-of-focus image is captured, regardless of whether a refractive aberration exists in the eye or other optical system being assessed. Here are three examples:

Consider a first example in which the light source is collimated, there is only one SLM, and that SLM is optically between the eye and the camera. In this example, a narrow light beam enters the eye, creates a spot in the retina, and then scatters back, passing through the lens and leaving the eye in a aberrated waveform. These aberrated rays are coded by the SLM and captured by the camera. In this example: (a) if the camera were focusing onto the retina, then the camera would not be able to see the pattern; and (b) a camera focusing onto the SLM would not be able to see the deformations of the pattern.

Or, consider a second example where the light source is not collimated, there is only one SLM, and the SLM is optically between the eye and the light source. In this example, a non collimated light beam crosses a SLM and enters the eye after being aberrated by the cornea and "prints" the aberrations to the retina. The camera focuses on the person's retina and captures the deformations of the pattern that are already there. However, the light that strikes the retina from the light source is out-of-focus, due to a lens system that is optically before the SLM and the light source. The optical power of the lens system prevents the eye from focusing on the SLM or the light source.

Or, consider a third example, where the light source is not collimated and two SLMs are used. In this example, a non-collimated light beam crosses a first coded SLM and enters the eye after being aberrated by the cornea and "prints" the aberrations to the retina. The light beam is out-of-focus when it strikes the retina, due to a lens system between the light source and the retina. The light from this pattern exits the eye and passes through a second coded SLM and reaches the out-of-focus camera. The captured image is then a convolution of the two codes. Advantageously, in this third example, neither the light nor the camera need to be in focus.

In exemplary implementations of this invention, the image of the SLM(s) that is captured is blurry and scaled (bigger) because it is out-of-focus. (This is similar to how an out-of-focus camera causes a single point source of light to spread out to become a blur circle that is bigger than the original point).

In exemplary implementations, one or more processors perform a compensation algorithm, to compensate for the scaling due to the out-of-focus aberrometer. For example, if the lack of focus in the aberrometer system itself causes a circle with radius x to expand to a circle with radius y, then the compensation algorithm would computationally scale the circle back down to radius x.

In exemplary implementations, the compensation algorithm scales the pattern in both horizontal and vertical directions by the same amount. The size of the blur circle of the camera is directly proportional to the size of the captured image. Defining an out of focus effect as the ratio of the distance from the camera's lens to the sensor (E) and the distance from the lens to the camera's image plane (S), and given a SLM with size A, the size of the captured pattern (I) is equal to: I=A(E/S)−A. Defining the camera as a thin lens system, the S is simply:

$$\frac{1}{S} = \frac{1}{f} - \frac{1}{O}$$

where f is the focal length of the lens and O is the distance from the lens to the object the camera is focusing at (e.g., infinity).

When E equals to S, the camera is in focus, and thus the image of the pattern has size zero. Thus, it can be preferable to have an out-of-focus camera. The bigger the camera's blur circle, the bigger the size of the captured pattern.

In exemplary implementations of this invention, one or more computer processors compute scaling, stretching and rotating operations. These operations are a set of geometric transformations (affine transformations) that can be defined in the form of a matrix that deform the captured image. Scaling transformations stretch or shrink a given image by a given factor for each axis. For instance, if the x-, y-axis are scaled with scaling factors p and q, respectively, the transformation matrix is:

$$\begin{bmatrix} x' \\ y' \end{bmatrix} = \begin{bmatrix} p & 0 \\ 0 & q \end{bmatrix} \begin{bmatrix} x \\ y \end{bmatrix}$$

Defocus aberrations may be re associated with a scaling matrix at which p and q are the same value. Astigmatism, on the other hand, may not only require p and q to be distinct numbers, but may also require a rotation if the axis of astigmatism is not 180 or 90 degrees, where the distortion aligns with the axes. The following matrix computes the rotation of the captured image of an angle (a), $$\begin{bmatrix} x' \\ y' \end{bmatrix} = \begin{bmatrix} \cos(a) & -\sin(a) \\ \sin(a) & \cos(a) \end{bmatrix} \begin{bmatrix} x \\ y \end{bmatrix}$$

Rotations occur around the origin, and so the method, before applying a certain rotation needs to find the center of the pattern and translate to that point. Once the central point of the SLM is found (Cx, Cy), the matrixes to rotate the pattern correctly can be joined into a composed transformation following (in homogenous coordinates):

$$\begin{bmatrix} x' \\ y' \\ z' \end{bmatrix} = \begin{bmatrix} 1 & 0 & -Cx \\ 0 & 1 & -Cy' \\ 0 & 0 & 1 \end{bmatrix} \begin{bmatrix} \cos(a) & -\sin(a) & 0 \\ \sin(a) & \cos(a) & 0 \\ 0 & 0 & 1 \end{bmatrix} \begin{bmatrix} 1 & 0 & Cx \\ 0 & 1 & Cy \\ 0 & 0 & 1 \end{bmatrix} \begin{bmatrix} x \\ y \\ 1 \end{bmatrix}$$

Adding all parameters together, the pattern captured from a patient with myopia or hyperopia and astigmatism is processed to find p, q, and a that satisfies the equation:

$$\begin{bmatrix} x' \\ y' \\ z' \end{bmatrix} = \begin{bmatrix} 1 & 0 & -Cx \\ 0 & 1 & -Cy' \\ 0 & 0 & 1 \end{bmatrix} \begin{bmatrix} p & 0 & 0 \\ 0 & q & 0 \\ 0 & 0 & 1 \end{bmatrix} \begin{bmatrix} \cos(a) & -\sin(a) & 0 \\ \sin(a) & \cos(a) & 0 \\ 0 & 0 & 1 \end{bmatrix} \begin{bmatrix} 1 & 0 & Cx \\ 0 & 1 & Cy \\ 0 & 0 & 1 \end{bmatrix} \begin{bmatrix} x \\ y \\ 1 \end{bmatrix}$$

After the image(s) have been captured and a compensation algorithm (described above) applied, the one or more computer processors may a wide variety of algorithms to compute the refractive condition (e.g., optical power) from the correlation of features between the original and distorted patterns. For example, the computations may be done busing (i) transformation matrices; (ii) matrix decomposition; (iii) geometric fitting over the distorted positions; or (iv) polar fitting over the distorted features.

For example, after the image(s) have been captured, and a compensation algorithm (described above), the one or more computer processors may analyze the captured images to find the features to be correlated with the original pattern. The farther the sampling is from the center of the image/pattern, the farther the algorithm is sampling from the center of the pupil. This allows the procedure to determine the corrective power for many pupil sizes by just varying the feature points for processing, which in turn will allow the measurement of higher-order aberrations such as coma or keratoconus. The bigger the amount of features correlated, the bigger the amount of diagonal components and thus the better the sampling over different angles in the eye. Sampling different angles allows for a better estimation of the axis of astigmatism.

If transformation matrixes from the feature positions are used: The image (S) captured by the sensor is the sensor SLM (M) deformed by the eye lens aberrations and can be formalized by S=DM, where D is, for low-order aberrations, a 2×2 linear transformation matrix that represents the deformation and is composed of geometric transformations including rotation, scaling and shearing, i.e., D=C*S*R. The rotational matrix R applies a rotation proportional to the axis and power of astigmatism, S shears the pattern proportionally to the cylinder and axis and the scaling matrix C scales proportionally to the spherical power and cylindrical powers. Using matrices to represent linear transformations permits easy composition and inversion of a plurality of transformations. In the matrix D, the scaling component is proportional to the optical power needed to correct for myopia, hyperopia or angular-dependent astigmatism and the rotation and shearing components are proportional to the axis of astigmatism.

If matrix decomposition from the feature displacements is used: A minimum of three feature points is typically required to compute an image transformation (warping) function (from the known pattern to the captured one). The three features are formulated as part of a system of equations: F'=DF, where the F and F' are the coordinates of the three equivalent features in the original and deformed patterns. D can be approximated by a linear system, although the system is non-linear if higher-order aberrations are found. There are several algorithms known to one of ordinary skill for solving a system of equations to find D, including the use of Radial Basis Functions. After D is found, mathematical solutions for matrix factorization such as principal component analysis and eigenvectors computation reduce the matrix to its minimum. For low-order aberrations, D may be further decomposed into C, S and R, thereby computing the spherical, cylindrical and axis of astigmatism. For higher-order aberrations, D can be transformed into a wavefront map, by refitting Zernike polynomials to the feature displacement dataset or by transforming D directly into a Zernike representation.

If geometric fitting over the position of the features is used: aberrations can be computed by using a best fitting function from the features that formed a known pattern in the original image. For instance, by selecting features from the pattern that are located on the circumference of a circle with a given radius, one can look for the same patterns with an ellipsoidal fitting function over the correlated feature positions on the captured image. The angle of the smaller radius of the ellipsoid is proportional to the axis of astigmatism. The smaller and bigger radiuses are proportional to the sphere and cylinder powers.

If sinusoidal fitting over the polar form of the position of the features is used: Features from the pattern that are located on the circumference of a circle with a given radius, when deformed by the eye, in the polar form, create a sinusoidal deformation. The distances from the features to the center of the pattern, after converted from pixels to optical powers, can be best fitted with a sinusoidal curve that defines an astigmatic lens, such as $P(t)=s+(c*\sin(a-t))$, where P(t) is the optical power from the distance of a given feature that is at an angle (t), s is the lens spherical power, c is the cylindrical power and a is the axis of astigmatism.

To measure high-order aberrations (keratoconus, coma, etc), a bigger sampling of features may be employed to compute the correlation between the distorted image and the original. A feature-based image warping technique using radial basis functions, for instance, can nicely create a mapping function between the original SLM and the captured one. A correlation of N feature points between both images should be used to generate a wavefront map of the patient's eye. The sampling strategy determines the resolution and accuracy of the method. The bigger the N, the bigger the resolution of the map.

By removing the eye and adding a test lens with a diffuser, another embodiment of this invention transforms the eye tester into a lensometer. This allows the measurement of the patient's eyesight and the quality of the current or new eye glasses.

Figure 9:
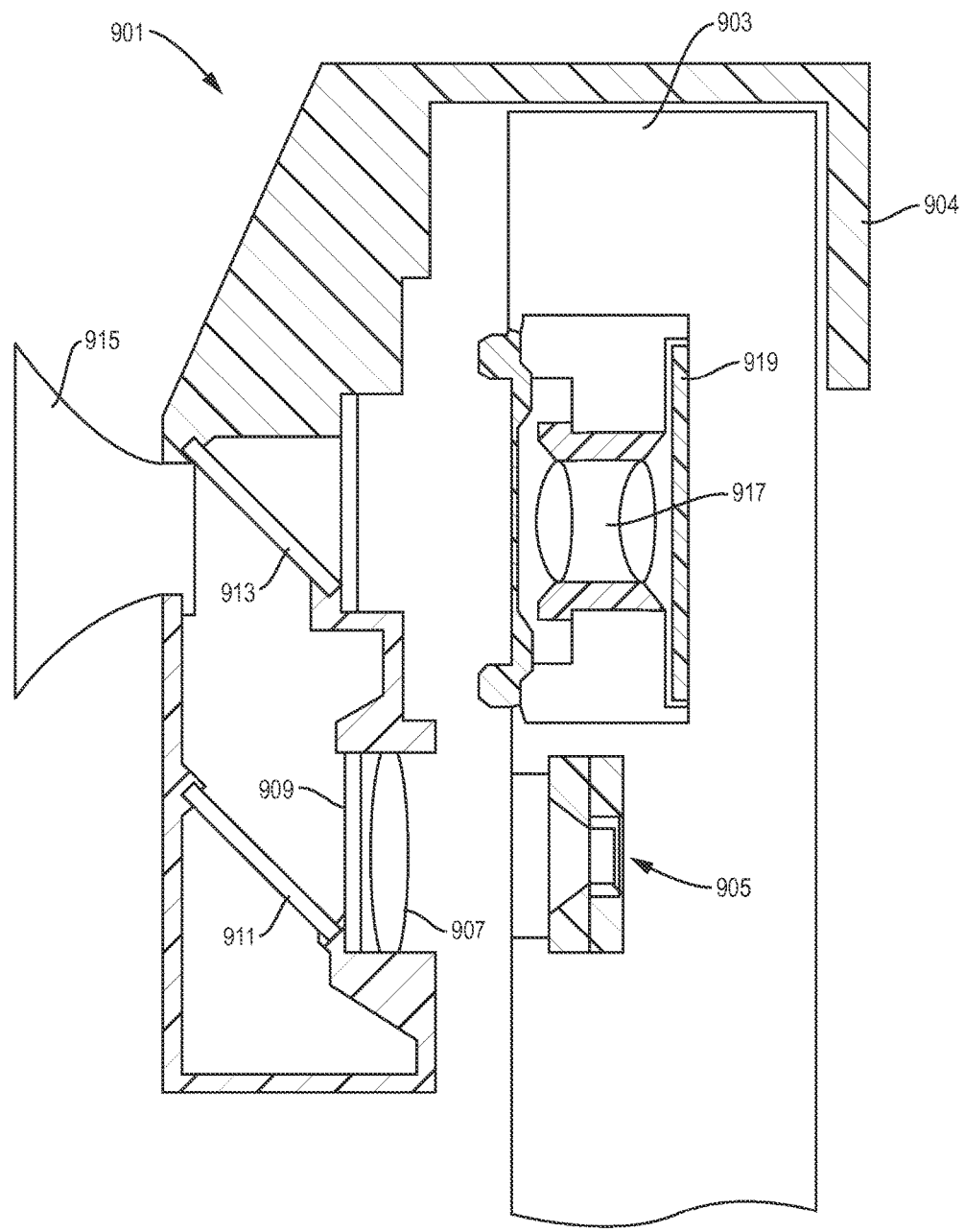
FIG. 9 is a cross-sectional view of an attachment that is attached to a mobile computing device.

FIG. 9 is a cross-sectional view of an attachment 901 that is attached to a mobile computing device (MCD) 903. A non-collimated light source (e.g., a flash for a camera) 905 is housed in the MCD. Alternately, the light source may be housed in the attachment 901, which may be preferable if the light source is a laser.

In the example shown in FIG. 9, an out-of-focus lens 907 causes the light from the flash, that passes through the coding SLM 909 to be out-of-focus for the eye that is seeing it. The out-of-focus system is preferred because if the system is in-focus the patient will only see a sharp point, which turns the coded light useless.

In the example shown in FIG. 9, the mobile computing device also houses a camera, including an objective lens-system 917 and an image sensor (light sensor) 919. The attachment includes a mirror 911 for steering the light from the flash, and a beamsplitter 913. The eyepiece 915 is configured to be pressed against the user's face and to keep the camera and SLM at a known distance from the eye being assessed.

The attachment 901 is configured to be releasably attached to the mobile computing device by a releasably attachable interface 904. Interface 904 in FIG. 9 (and attachment mechanism 1119 in FIG. 11) each symbolically represent any attachment mechanism, including any implementation of the following approaches: (1) the attachment 901 may include a clip to clip over the MCD 903; (2) the attachment 901 may include one or more flexible bands that wrap around the MCD 903; (3) the attachment 901 may include an opening that grabs the MCD 903 on at least two edges or corners by retention features; (4) the attachment 901 may include a slot or other indentation into which the MCD 903 may be inserted; (5) the attachment 901 may include an opening with a socket into which the MCD 903 may be partially or fully inserted; or (6) the attachment 901 may include a door or flap that can be opened and closed via a hinge that covers a socket or bedding for the MCD 903.

Figure 10:
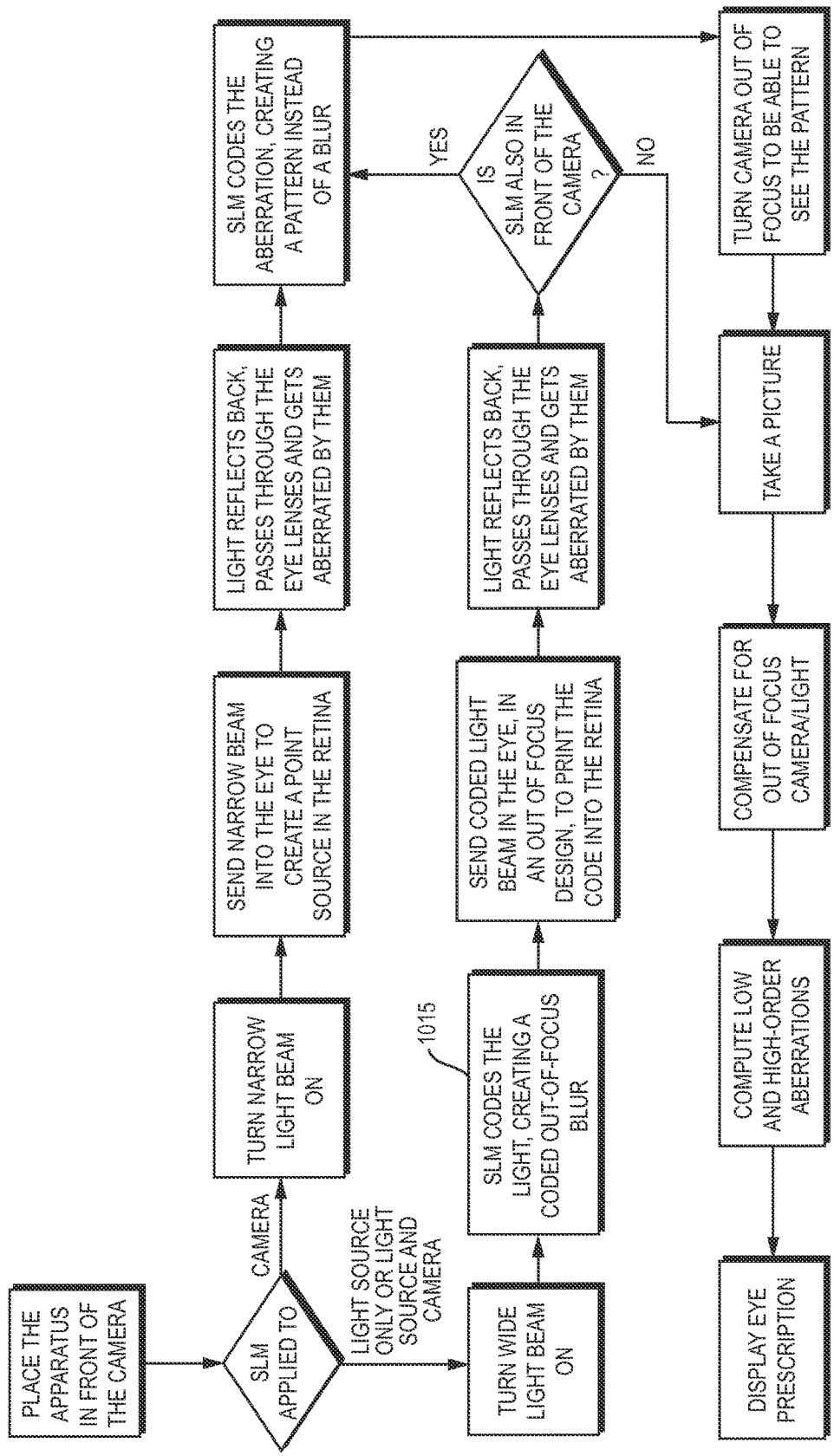
FIG. 10 is a flowchart which shows steps in a process for measuring optical aberrations of the eye.

FIG. 10 is a flowchart which shows steps in a process for measuring optical aberrations of the eye. The steps include using an SLM (e.g., mask) to code the light 1015.

Figure 11:
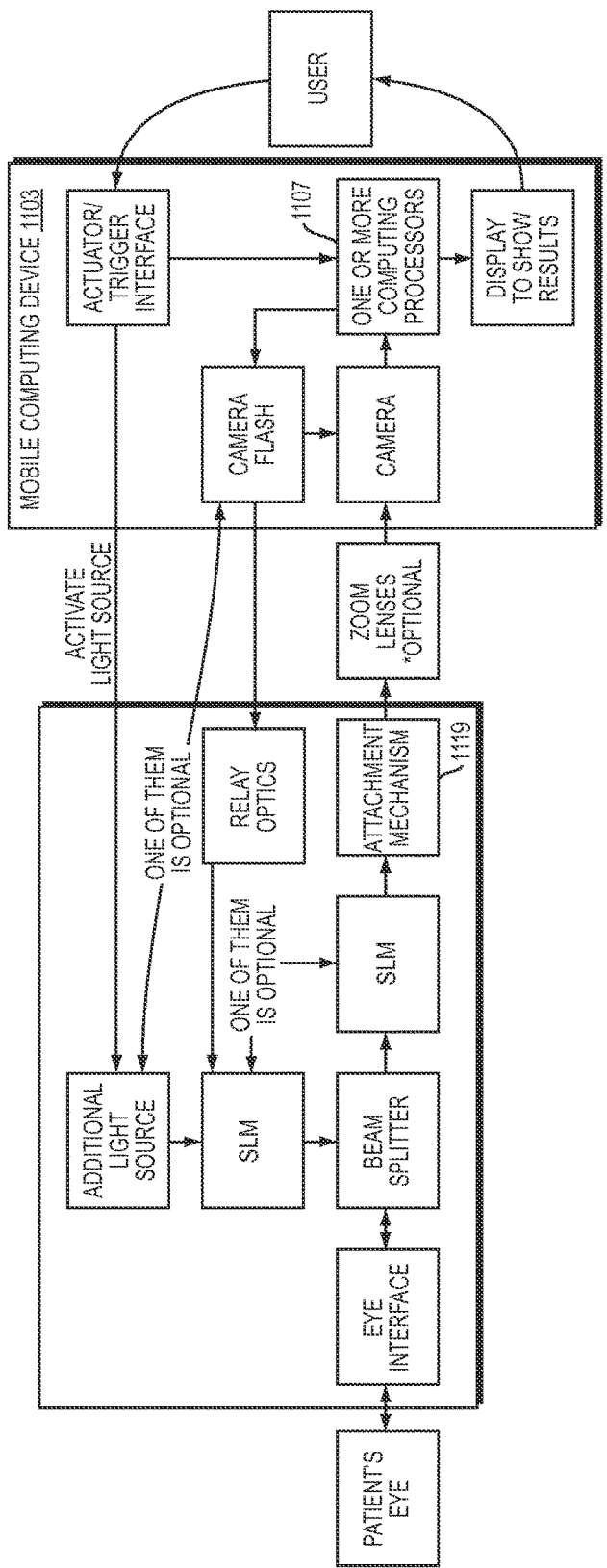
FIG. 11 is a conceptual diagram that show some features of an illustrative embodiment of this invention.

FIG. 11 is a conceptual diagram that show some features of an illustrative embodiment of this invention. One or more computer processors 1107 are housed in a mobile computing device 1103.

Figure 12:
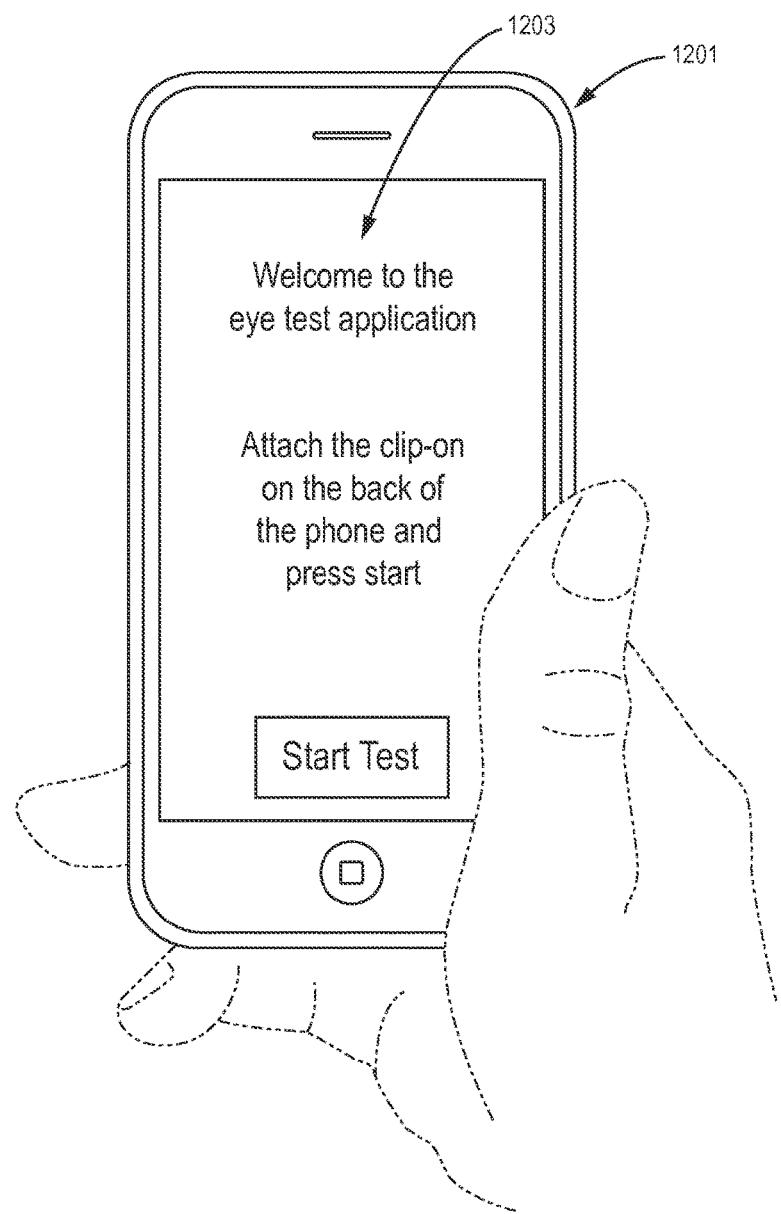
FIGS. 12, 13, and 14 show examples of images displayed by a graphical user interface (GUI) on a mobile computing device, in an exemplary implementation of this invention.
Figure 13:
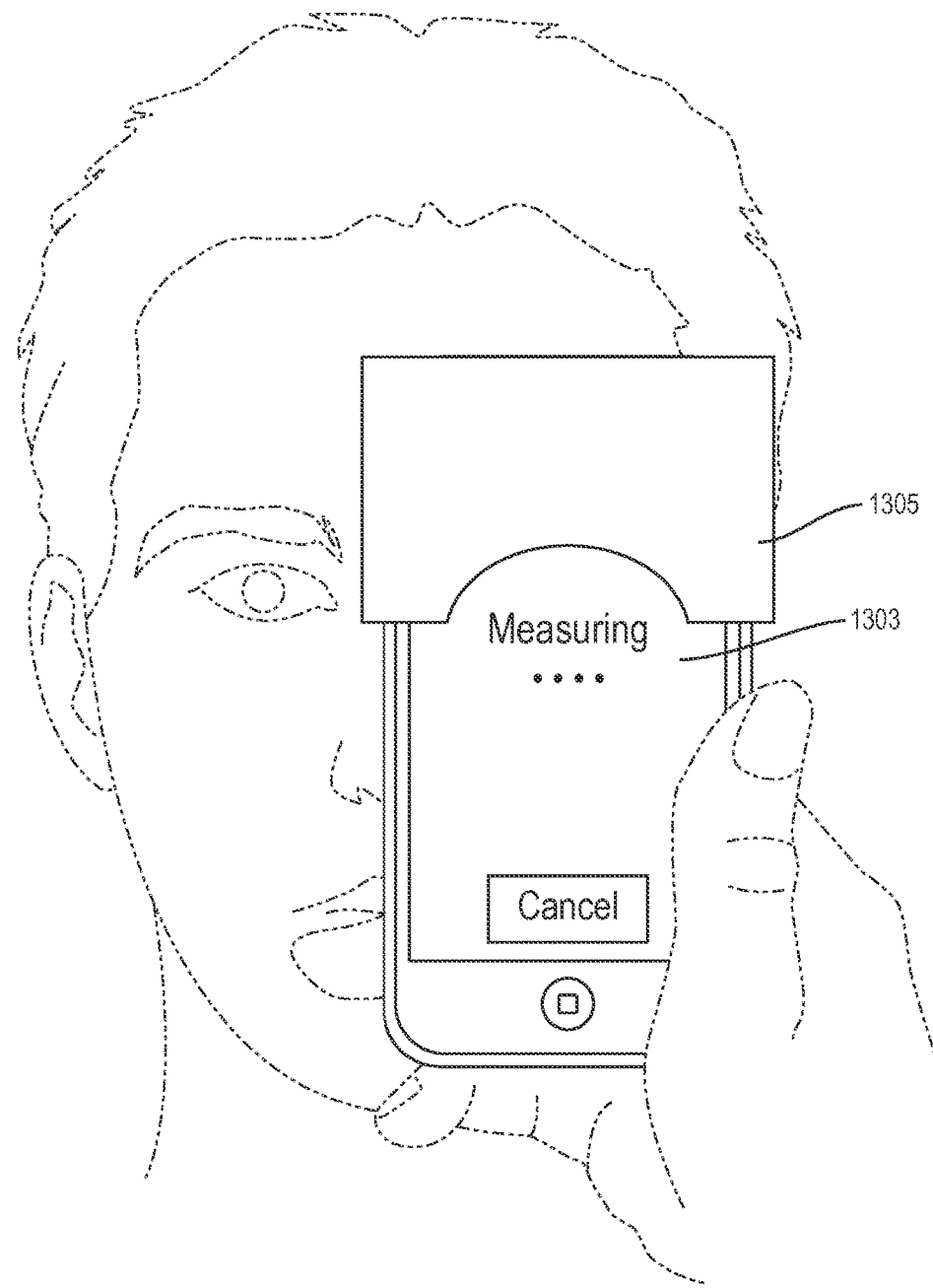
Figure 14:
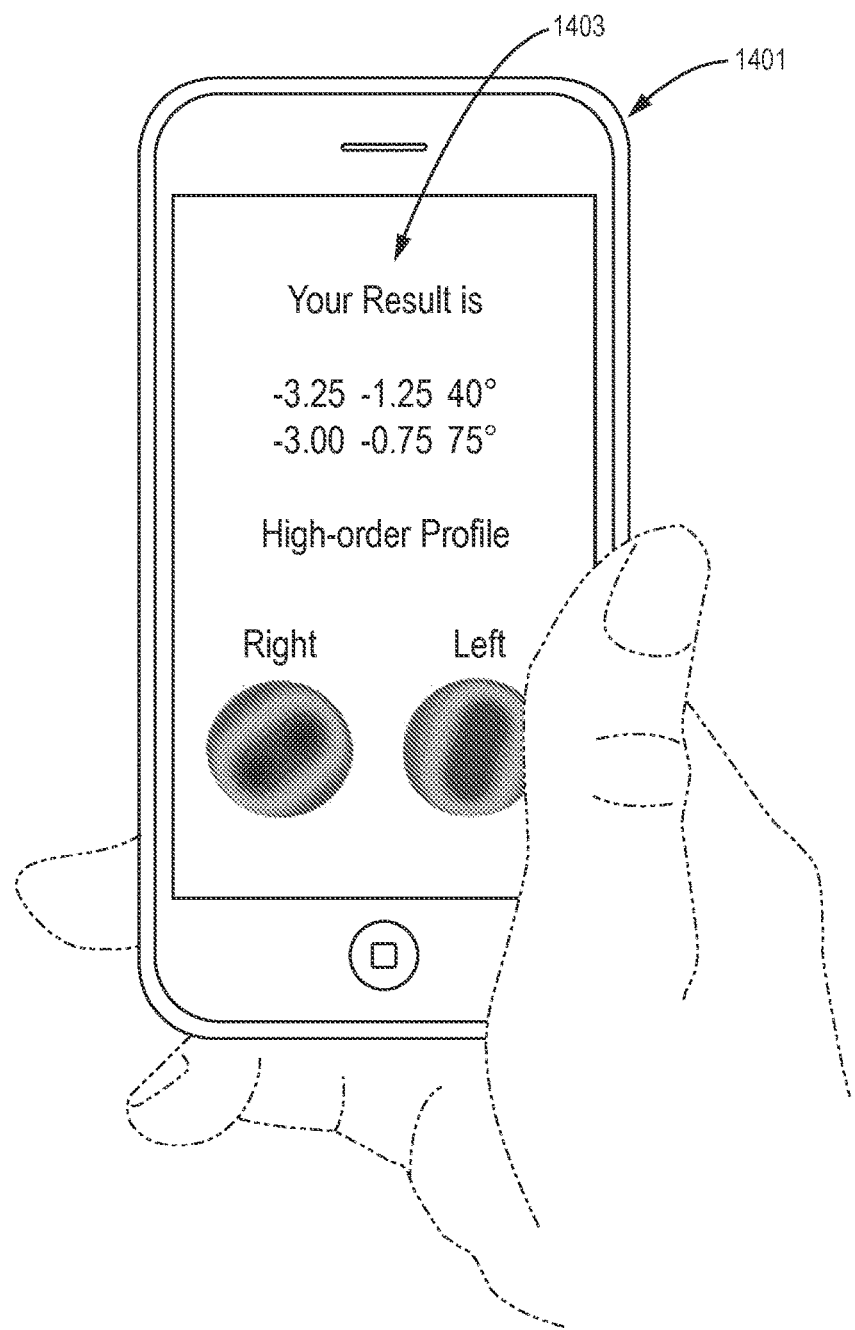

FIGS. 12, 13, and 14 show examples of images displayed by a graphical user interface (GUI) 1203, 1303, 1403 on a mobile computing device 1201, 1401, in an exemplary implementation of this invention. In FIG. 12, the GUI displays a "Welcome to the eye test application" message. In FIG. 13, the GUI displays a message indicating that the eye test is in progress. An attachment 1305 houses an SLM being used in the eye test. In FIG. 14, the GUI displays eye test results.

In exemplary implementations of this invention, one or more electronic processors are specially adapted: (1) to control the operation of hardware components of aberrometer, including any light source, any SLM, any light sensor, any actuator for changing focal length, and any component of a mobile computing device, (2) to perform compensation calculations to compensate for scaling due to an out-of-focus aberrometer; (3) to perform calculations to identify visual patterns and to calculate differences (e.g., transformations) between a distorted image and an original, undistorted image; (4) to calculate a refractive condition or to calculate prescription for eyewear; (5) to receive signals indicative of human input, (6) to output signals for controlling transducers for outputting information in human perceivable format, and (7) to process data, perform computations, and control the read/write of data to and from memory devices. The one or more processors may be located in any position or position within or outside of the aberrometer. For example: (a) at least some of the one or more processors may be embedded within or housed together with a mobile computing device that is attached to or part of the aberrometer, and (b) at least some of the one or more processors may be remote from other components of the aberrometer, including the mobile computing device. The one or more processors may be connected to each other or to other components in the light field camera either: (a) wirelessly, (b) by wired connection, or (c) by a combination of wired and wireless connections. For example, one or more electronic processors (e.g., 1107) may be housed in a computer in a mobile computing device.

Definitions:

Here are a few definitions and clarifications. As used herein:

The terms "a" and "an", when modifying a noun, do not imply that there is only one of the noun. For example, if there is "a" SLM along an optical path, then there are one or more SLMs on the optical path.

The term "aberrometer" means any apparatus for measuring the refractive condition of an optical system (e.g., the refractive condition of a human eye).

The term "comprise" (and grammatical variations thereof) shall be construed broadly, as if followed by "without limitation". If A comprises B, then A includes B and may include other things.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each can be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes "a third" thing, a "fourth" thing and so on shall be construed in like manner.

As used herein, the noun "focus" means optical focus involving converging light rays. The verb "focus" shall be construed in the same manner. As used herein, the term "focus" does not mean merely paying attention or altering direction of gaze.

In the context of a camera (or components of the camera), "front" is optically closer to the scene being imaged, and "rear" is optically further from the scene, during normal operation of the camera. In the context of a display device (or components of the display device), "front" is optically closer to a human viewer, and "rear" is optically further from the viewer, when the viewer is viewing a display produced by the device during normal operation of the device. The "front" and "rear" of a display device continue to be the front and rear, even when no viewer is present.

The terms "horizontal" and "vertical" shall be construed broadly. For example, "horizontal" and "vertical" may refer to two arbitrarily chosen coordinate axes in a Euclidian two dimensional space.

The term "include" (and grammatical variations thereof) shall be construed broadly, as if followed by "without limitation".

"Intensity" means any measure of or related to intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure and radiant energy density.

The term "lens-system" means a device comprising one or more lens. For example, an objective lens-system may comprise a single objective lens or may comprise a group of multiple objective lenses.

The term "light" means electromagnetic radiation of any frequency. For example, "light" includes, among other things, visible light and infrared light. Likewise, any term that directly or indirectly relates to light (e.g., "imaging") shall be construed broadly as applying to electromagnetic radiation of any frequency.

The term "matrix" includes a matrix that has two or more rows, two or more columns, and at least one non-zero entry. The term "matrix" also includes a vector that has at least one non-zero entry and either (a) one row and two or more columns, or (b) one column and two or more rows. However, as used herein, (i) a scalar is not a "matrix", and (ii) a rectangular array of entries, all of which are zero (i.e., a so-called null matrix), is not a "matrix".

The term "mobile computing device" or "MCD" includes any of the following electronic devices: a smartphone, cell phone, mobile phone, phonepad, tablet, laptop, notebook, notepad, personal digital assistant, enterprise digital assistant, ultra-mobile PC, or any handheld computing device. A device may be an MCD even if it is not configured for direct or indirect connection to an internet or world wide web.

To "multiply" includes to multiply by an inverse. Thus, to "multiply" includes to divide.

The term "or" is inclusive, not exclusive. For example A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or can be ignored.

To compute a term that "satisfies" an equation: (a) does not require that calculations involve terms, variables or operations that are in the equation itself, as long as the term itself (subject to error, as described in part (b) of this sentence) is computed; and (b) includes computing a solution that differs from a correct solution by an error amount, which error amount arises from one or more of (i) rounding, (ii) other computational imprecision, including error due to modeling a continuous signal by a discrete signal or due to using an insufficiently small step size in calculations, and (iii) signal noise or other physical limitations of sensors or other physical equipment.

As used herein, the term "set" does not include a so-called empty set (i.e., a set with no elements).

A "spatial light modulator", also called an "SLM", is a device that (i) either transmits light through the device or reflects light from the device, and (ii) attenuates such light, such that the attenuation of light incident at a point on a surface of the device depends on at least the 2D spatial position of the point on the surface. For example, the attenuation pattern may be the same for all frequencies of light. Or, for example, the attenuation pattern may vary, depending on the frequency of the light. For example, a SLM may comprise an optical mask. However, an array of lenslets is not an SLM. An SLM may be in the same optical path as an array of lenslets; but an array of lenslets is not, itself, an SLM.

As used herein, a "subset" of a set consists of less than all of the elements of the set.

The term "such as" means for example.

A matrix may be indicated by a bold capital letter (e.g., D). A vector may be indicated by a bold lower case letter (e.g., a). However, the absence of these indicators does not indicate that something is not a matrix or not a vector.

Unless the context clearly indicates otherwise, any term, phrase or other reference to an optical device (e.g., a lens) applies also to a functionally equivalent optical device. For example, any optical device with two surfaces in an optical path may be alternatively implemented with multiple surfaces in the optical path. For example, a single functional "lens" may be implemented as a set of multiple lenses.

A "Defined Term" means a term that is set forth in quotation marks in this Definitions section. Applicant is acting as his, her or its own lexicographer for the Defined Terms. This Definitions section shall, in all cases, control over and override any other definition of the Defined Terms. For example, the definitions of Defined Terms set forth in this Definitions section override common usage or any external dictionary.

If a given term is explicitly or implicitly defined in this document, then that definition shall be controlling, and shall override any definition of the given term arising from any source (e.g., a dictionary or common usage) that is external to this document.

If this document provides clarification regarding the meaning of a particular term, then that clarification shall, to the extent applicable, override any definition of the given term arising from any source (e.g., a dictionary or common usage) that is external to this document.

Variations:

This invention may be implemented in many different ways, in addition to those described above.

Here are some non-limiting examples of how this invention may be implemented:

This invention may be implemented as a method of measuring a refractive condition of an eye, which method comprises, in combination: (a) emitting light from an artificial light source, such that (i) the light travels along a set of optical paths, which each start at the light source and end at a light sensor, and each enter and then exit the eye, (ii) the light passes through or is reflected from one or more SLMs, including a first SLM that is optically positioned between the light sensor and the eye, and (iii) the light passes through an objective lens-system that is optically between the eye and the light sensor; (b) using the light sensor to capture one or more images; and (c) using one or more processors (i) to determine differences between a first visual pattern and a second visual pattern, the first visual pattern being based at least in part on a pattern that appears in at least one of the images, and the second visual pattern being based at least in part on a pattern displayed by the first SLM, and (ii) to compute the refractive condition, based at least in part on the differences; wherein (1) the light sensor and each and every optical element that is optically between the light sensor and the eye together comprise a camera, and (2) the camera is not focused on the first SLM and is not focused on the retina of the eye. Furthermore: (1) a second SLM may be optically positioned between the light source and the eye; (2) the light may pass through a second lens system that is optically between the light source and the eye and is optically in front of the second SLM, and the lens system may have an optical power that prevents the eye from focusing on the second SLM and from focusing on the light source; (4) the objective lens-system, the light sensors, and the one or more processors may be housed in a mobile computing device; (5) the first SLM may be housed in a device that is releasably attached to the mobile computing device; (6) the refractive condition may be myopia, hyperopia or astigmatism; and (7) the refractive condition may be keratoconus, optical coma, trefoil or another high-order refractive aberration.

This invention may be implemented as a method of measuring a refractive condition of an eye, which method comprises, in combination: (a) emitting light from an artificial light source, such that (i) the light travels along a set of optical paths, which each start at the light source and end at a light sensor, and each enter and then exit the eye, (ii) the light passes through or is reflected from one or more SLMs, including a first SLM that is optically positioned between the light source and the eye, and (iii) the light passes through a first lens system that is optically between the light source and the eye and that is optically in front of the first SLM; (b) using the light sensor to capture one or more images; and (c) using one or more processors (i) to determine distortion of a first visual pattern relative to a second visual pattern, the first visual pattern being based at least in part on a pattern that appears in at least one of the images, and the second visual pattern being based at least in part on a pattern displayed by the first SLM, and (ii) to compute the refractive condition, based at least in part on the distortion; wherein the optical power of the first lens system is such that the eye cannot focus on the first SLM and cannot focus on the light source. Furthermore: (1) an objective lens-system may be optically between the eye and the light sensor; (2) the objective lens-system, the light sensor and the one or more processors may be housed in a mobile computing device; (3) the first SLM may be housed in a device that is releasably attached to the mobile computing device; (4) the refractive condition may be myopia, hyperopia or astigmatism;and (5) the light may pass through more than one SLM.

This invention may be implemented as a method of measuring refractive condition of an eye, which method comprises, in combination: (a) emitting light from an artificial light source, such that at least part of the light (i) travels along a set of optical paths that each start at the light source and end at a light sensor, and each enter and then exit the eye, (iii) passes through or is reflected from one or more SLMs, including a first SLM, and (iv) passes through an objective lens-system that is optically between the eye and the light sensor; (b) using the light sensor to capture one or more images; and (c) using one or more processors (i) to determine differences between a first visual pattern and a second visual pattern, the first visual pattern being based at least in part on a pattern that appears in at least one of the images, and the second visual pattern being based at least in part on a pattern displayed by the first SLM, and (ii) to compute the refractive condition, based at least in part on the differences. Furthermore, the first SLM may be optically positioned between the light sensor and the eye.

This invention may be implemented as apparatus comprising, in combination: (a) an SLM, and (b) a structure that (i) houses and mechanically supports the SLM, and (ii) is configured to be releasably attached to a mobile computing device, which mobile computing device is configured to take a photograph of an eye of a human when (A) the attachment is pressed against the human, (B) the camera is not focused on the SLM, (C) the camera is not focused on the retina of the eye, and (D) the light being captured in the photograph has passed through the SLM. Furthermore: (1) the apparatus may further comprises a light source for emitting collimated light; (2) the structure may be configured to keep the SLM at a distance from the eye when the structure is pressed against a region of the user's face; (3) the SLM may be configured to display a light attenuation pattern that does not vary over time; (4) the SLM may be configured to display a light attenuation pattern that varies over time; and (5) the SLM may include color filters, polarizing filters and optical coatings.

CONCLUSION

While exemplary implementations described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention. Numerous modifications may be made by one of ordinary skill in the art without departing from the scope of the invention.

What is claimed is:

1. A method comprising:
   (a) capturing, with a light sensor, an unfocused image of a first spatial light modulator (SLM), which unfocused image is formed by light that has entered and exited an eye and then passed through a first lens-system;
   (b) analyzing differences between a first visual pattern and a second visual pattern; and
   (c) computing a refractive aberration of the eye, based at least in part on the differences;
   wherein
   (1) the first SLM is positioned optically between the eye and the light sensor,
   (2) the first visual pattern comprises the unfocused image or comprises a transformation of the unfocused image,
   (3) the second visual pattern comprises a second image of the first SLM that is not distorted by the refractive aberration of the eye,
   (4) an artificial light source emits the light,
   (5) a second SLM is positioned optically between the light source and the eye,
   (6) the light passes through a second lens system that is optically between the light source and the eye, and
   (7) the second lens system has an optical power that prevents the eye from focusing on the second SLM and from focusing on the light source.

2. The method of claim 1, wherein:
   (a) the light sensor is housed in a mobile computing device; and
   (b) the first lens-system is located in the mobile computing device.

3. The method of claim 2, wherein the first SLM is housed in a device that is releasably attached to the mobile computing device.

4. The method of claim 1, wherein the refractive aberration is myopia, hyperopia or astigmatism.

5. The method of claim 1 wherein the refractive aberration is keratoconus, optical coma, or trefoil.

6. The method of claim 1, wherein the light is in a collimated state before it enters the eye.

7. The method of claim 1, wherein the light is in an uncollimated state immediately before the light enters the eye.

8. A method comprising:
   (a) capturing, with a light sensor, an unfocused image of a spatial light modulator (SLM), which unfocused image is formed by light that has entered and then exited an eye and then passed through a lens-system;
   (b) analyzing differences between a first visual pattern and a second visual pattern; and
   (c) computing a first refractive aberration of the eye, based at least in part on the differences;
   wherein
   (1) the SLM is positioned optically between the eye and an artificial light source that emits the light,
   (2) the first visual pattern comprises the unfocused image or comprises a transformation of the unfocused image,
   (3) the second visual pattern comprises a second image of the SLM that is not distorted by the first refractive aberration of the eye, and
   (4) the unfocused image is unfocused due to reasons other than the first refractive aberration and other than any other refractive aberration of the eye.

9. The method of claim 8, wherein:
   (a) the light passes through a second lens-system after exiting the light source and before entering the eye; and
   (b) the second lens-system refracts the light in such a way that the eye cannot focus on the SLM and cannot focus on the light source.

10. The method of claim 8, wherein:
    (a) the light sensor is housed in a mobile computing device; and
    (b) the lens-system that is mentioned in claim 8 is located in the mobile computing device.

11. The method of claim 8, wherein the refractive aberration is myopia, hyperopia or astigmatism.

12. The method of claim 8, wherein the refractive aberration is keratoconus, optical coma, or trefoil.

13. The method of claim 8, wherein the light is in an uncollimated state immediately before the light enters the eye.

14. The method of claim 8, wherein the SLM is housed in a device that is releasably attached to the mobile computing device.

* * * * *